(12) United States Patent
Gounder et al.

(10) Patent No.: US 11,517,888 B2
(45) Date of Patent: Dec. 6, 2022

(54) NICKEL-BASED MICROPOROUS AND MESOPOROUS CATALYSTS FOR SELECTIVE OLEFIN OLIGOMERIZATION

(71) Applicant: PURDUE RESEARCH FOUNDATION, West Lafayette, IN (US)

(72) Inventors: Rajamani Gounder, West Lafayette, IN (US); Ravi Joshi, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 16/635,648

(22) PCT Filed: Jul. 31, 2018

(86) PCT No.: PCT/US2018/044605
§ 371 (c)(1),
(2) Date: Jan. 31, 2020

(87) PCT Pub. No.: WO2019/028022
PCT Pub. Date: Feb. 7, 2019

(65) Prior Publication Data
US 2021/0129121 A1    May 6, 2021

Related U.S. Application Data

(60) Provisional application No. 62/545,977, filed on Aug. 15, 2017, provisional application No. 62/539,742, filed on Aug. 1, 2017.

(51) Int. Cl.
| | |
|---|---|
| C07C 2/24 | (2006.01) |
| B01J 29/072 | (2006.01) |
| B01J 37/30 | (2006.01) |
| B01J 29/76 | (2006.01) |
| B01J 37/08 | (2006.01) |

(52) U.S. Cl.
CPC ......... B01J 29/7615 (2013.01); B01J 29/072 (2013.01); B01J 37/088 (2013.01);
(Continued)

(58) Field of Classification Search
None
See application file for complete search history.

(56) References Cited

U.S. PATENT DOCUMENTS

| | | |
|---|---|---|
| 4,487,847 A | 12/1984 | Knudsen |
| 4,942,021 A | 7/1990 | Garwood et al. |

(Continued)

FOREIGN PATENT DOCUMENTS

WO    WO-2007068752 A1 *  6/2007  ............. C10G 50/00

OTHER PUBLICATIONS

English Translation of WO 2007/068752 A1 obtained from Espacenet, Apr. 20, 2021, pp. 1-16 (Year: 2021).*
(Continued)

*Primary Examiner* — Philip Y Louie
(74) *Attorney, Agent, or Firm* — Edmonds & Cmaidalka, P.C.

(57) ABSTRACT

A novel catalyst composition and its use in the oligomerization reaction converting a portion of a $C_4$ to $C_{5+}$ alkene feed stream to $C_4$ to $C_{6+}$ olefin derivatives. The catalyst comprises a Group VIII metal selected from the group consisting of nickel, iron, cobalt, and combinations thereof, on a support. The support can be silica, silicon dioxide, titanium dioxide, metal modified silica, silica-pillared clays, silica-pillared micas, metal oxide modified silica-pillared mica, silica-pillared tetrasilicic mica, silica-pillared taemolite, zeolite, molecular sieve, and combinations thereof. The catalyst composition is an active and selective catalyst for the catalytic oligomerization of alkenes to olefins and olefin derivatives.

27 Claims, 19 Drawing Sheets

(52) U.S. Cl.
CPC .......... *C07C 2/24* (2013.01); *C07C 2523/755* (2013.01); *C07C 2529/78* (2013.01)

(56) References Cited

U.S. PATENT DOCUMENTS

2011/0124938 A1* 5/2011 Inoue .................. B01J 38/14
585/533
2011/0282123 A1 11/2011 Corma et al.

OTHER PUBLICATIONS

Deimund et al., Nickel-Exchanged Zincosilicate Catalysts for the Oligomerization of Propylene, ACS Catalysis, 2014, p. 4189-4195. (Year: 2014).*

International Search Report and Written Opinion for International Application No. PCT/US2018/044605 dated Oct. 1, 2018.

Deimund, M.A.; I. Nickel-Exchanged Zincosilicate Catalysts for the Oligomerization of Propylene and II. Organic SDA-Free Catalysts for the Methanol-to-Olefins Reaction; California Institute of Technology; 2015; pp. 8, 13-14, 17, 20, 234; [retrieved on Sep. 13, 2018]; Retrieved from the Internet <URL: https://search.proquest.com/openview/79c8794e212beac1099bcedb9eff089e/1?pq-origsite=gscholar&cbl=18750&diss=y>.

Sounder, R. et al.; Catalytic Alkylation Routes via Carbonium-Ion-Like Transition States on Acidic Zeolites; ChemCatChem.; Jul. 11, 2011; vol. 3, No. 7; fifth page, tenth page, Scheme S. 1.

Pookote, S.R.; Cyclohexene hydrogenation on deactivated hydrocracking catalysts; Dissertation; Northwestern University; 1981; pp. 15 and 35.

* cited by examiner

The exchange of one extraframework $Ni^{2+}$ site requires two framework $Al^{3+}$ centers in a paired configuration (left; aluminosilicate) or one framework $Zn^{2+}$ center (right; zincosilicate).

Net butene formation rate vs. time-on-stream for a) Ni-Li-[Al]BEA and b) Ni-Li-[Zn]BEA, measured at 453 K and 0.2 kPa ethene on fresh sample (○) and after treatment in 5%O2/He at 803 K for 4 hours (●).

XRD patterns of (a) As-made Li-[Zn]BEA, (b) SDA free Li-[Zn]BEA and (c) As-made VPI-8

SEM image for as-made Li-[Zn]BEA

XRD patterns of (a) Bulk NiO, (b) NiO/Si-BEA, (c) SDA free Li-[Zn]BEA, (d) Ni-Li-[Zn]BEA, and (e) Ni-H-[Al]BEA (A) UV-vis spectra at 290 K for (a) Ni-H-[Al]BEA, (b) Ni-Li-[Zn]BEA and (c) Ni-Li-[Al]BEA under hydrated conditions. (B) UV-vis spectra at 290 K for (a) Ni-H-[Al]BEA, (b) Ni-Li-[Zn]BEA and (c) Ni-Li-[Al]BEA after dehydration.

IR spectra collected for successive CO doses and saturated spectrum (thick line) for Ni-Li-[Al]BEA at 243 K. Dashed reference lines shown for the absorption features at 2212, 2206, 2196, 2185, 2162, 2157 and 2112 $cm^{-1}$.

IR spectra collected for successive pyridine doses and saturated spectrum (thick line) for Li-[Zn]BEA at 423 K. Dashed reference lines shown for Lewis acid sites (1451, 1491, 1610 cm-1) and for hydrogen-bonded physisorbed pyridine (1444, 1575 cm-1).

Fig. 10

(A) Ethene conversion at 453 K and 0.4 kPa ethene for oxidatively pretreated Ni-Li-[Zn]BEA (●), H-[Al]BEA (◇), Ni-Li-[Al]BEA (■) and Ni-H-[Al]BEA (▲). The conversion was measured at a different space velocity for each catalyst. Dashed line (---) represents 1.4% conversion for [Al]BEA catalysts on the primary y-axis. (B) Ethene conversion at 453 K, 0.4 kPa ethene and 0.35 mol ethene $s^{-1}$ (mol Ni)$^{-1}$ for non-pretreated Ni-Li-[Al]BEA (■) and $NH_3$ poisoned Ni-Li-[Al]BEA (□).

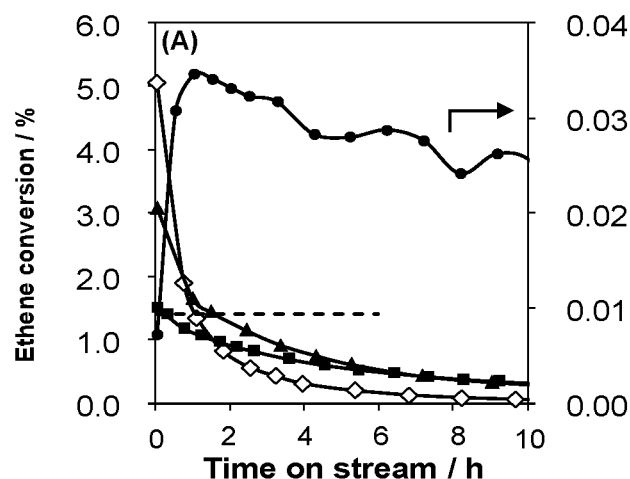

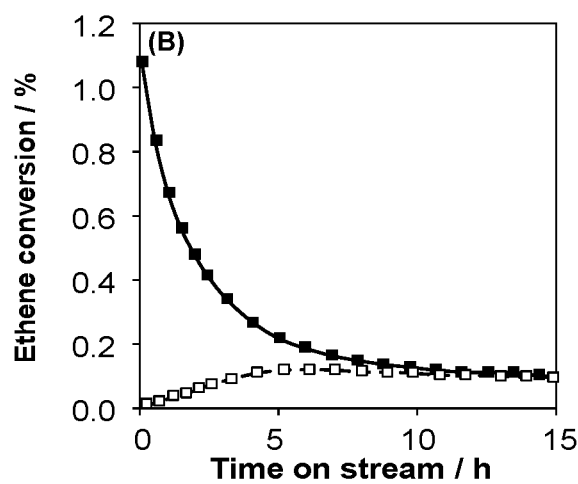

Molar selectivity comparison between oxidatively pretreated H-[Al]BEA (1.4% conv.), Ni-H-[Al]BEA (1.4% conv.), Ni-Li-[Al]BEA (1.4% conv.), Ni-Li-[Zn]BEA (0.035% conv.) and non-pretreated Ni-Li-[Al]BEA poisoned with $NH_3$ (0.1% conv.)

Linear butene isomer distribution for oxidatively pretreated H-[Al]BEA (1.4% conv.), Ni-H-[Al]BEA (1.4% conv.), Ni-Li-[Al]BEA (1.4% conv.), Ni-Li-[Zn]BEA (0.035% conv.) and non-pretreated Ni-Li-[Al]BEA poisoned with NH₃ (0.1% conv.)

Fig. 13

Transient 2-butenes/1-butene (filled symbols) and isobutene/1-butene (unfilled symbols) ratios for H-[Al]BEA (▲) (0.005 mol ethene s$^{-1}$ (mol H$^+$)$^{-1}$) and Ni-Li-[Al]BEA (■) (0.39 mol ethene s$^{-1}$ (mol Ni)$^{-1}$), at 453 K and 0.4 kPa ethene pressure. Transient 2-butenes/1-butene ratio for Ni-Li-[Zn]BEA (●) (0.09 mol ethene s$^{-1}$ (mol Ni)$^{-1}$) at 453 K and 0.7 kPa ethene pressure. Calculated equilibrium distribution at 453 K (-----), asymptotic value for Ni-Li-[Al]BEA (− · − ·) and asymptotic value for Ni-Li-[Zn]BEA (·······).

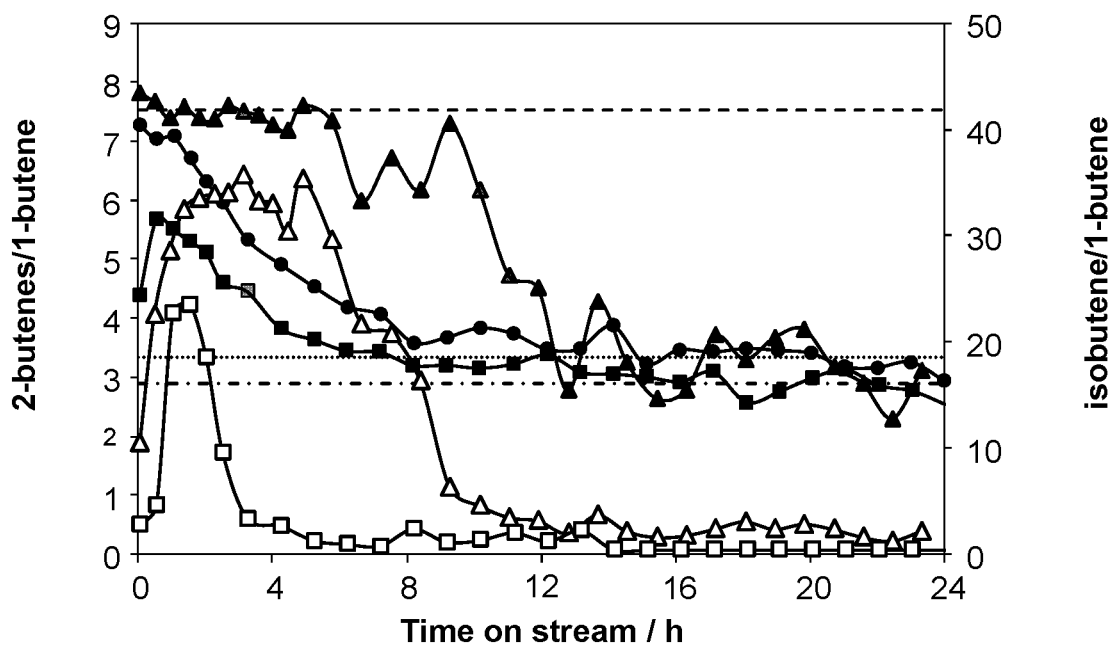

Effect of space time on 2-butenes/1-butene ratio for Ni-Li-[Al]BEA at 453 K, 0.2 kPa pressure and measured at a reaction time of 0.5 hour.

Effect of space time on non-equilibrium distribution of linear butene isomers on Ni intermediates at 453 K for Ni-Li-[Al]BEA (■) at 0.2 kPa, and Ni-Li-[Zn]BEA (●) at 0.7 kPa. Calculated equilibrium distribution [29] at 453 K (-----), asymptotic value for Ni-Li-[Al]BEA (– · – ·) and asymptotic value for Ni-Li-[Zn]BEA (·······), adapted from Figure 7.

Fig. 16
(A) Transient net butene formation rate at 453 K for Ni-Li-[Al]BEA (■) at 0.1 kPa and Ni-Li-[Zn]BEA (●) at 0.4 kPa.   (B) Dependence of the duration of activation period on ethene partial pressure for Ni-Li-[Al]BEA (■) and Ni-Li-[Zn]BEA (●).
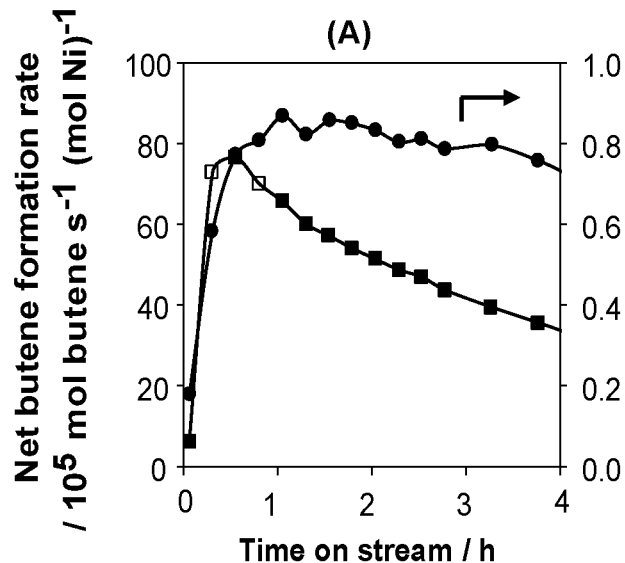
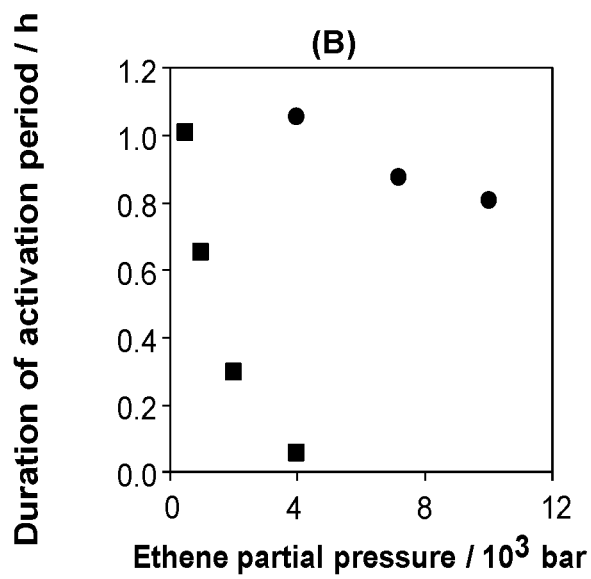

(A) Transient net butene formation rate (■) and 2-butenes/1-butene ratio for Ni-Li-[Al]BEA (453 K, 0.05 kPa, 0.02 mol ethene s$^{-1}$ (mol Ni)$^{-1}$). Thermodynamic equilibrium distribution at 453 K (-----). (B) Transient net butene formation rate (■) and isobutene formation rate for Ni-Li-[Al]BEA (453 K, 0.05 kPa, 0.02 mol ethene s$^{-1}$ (mol Ni)$^{-1}$).

(A) Comparison between the transients for net butene formation rate and 2-butenes/1-butene ratio. (B) Comparison between the transients for net butene formation rate and isobutene formation rate.

Comparison between the transients for net butene formation rate and 2-butenes/1-butene ratio.

Fig. 20

Hyperbolic deactivation model fitted to the initial transient of the net butene formation rate measured on Ni-Li-[Al]BEA at 453 K, 0.4 kPa ethene pressure and space velocity of 0.35 mol ethene (mol Ni)$^{-1}$ s$^{-1}$. $r_o$ is the initial net butene formation rate, k is the apparent deactivation rate constant and n is the order dependence of the deactivation rate w.r.t. the number of un-poisoned active sites.

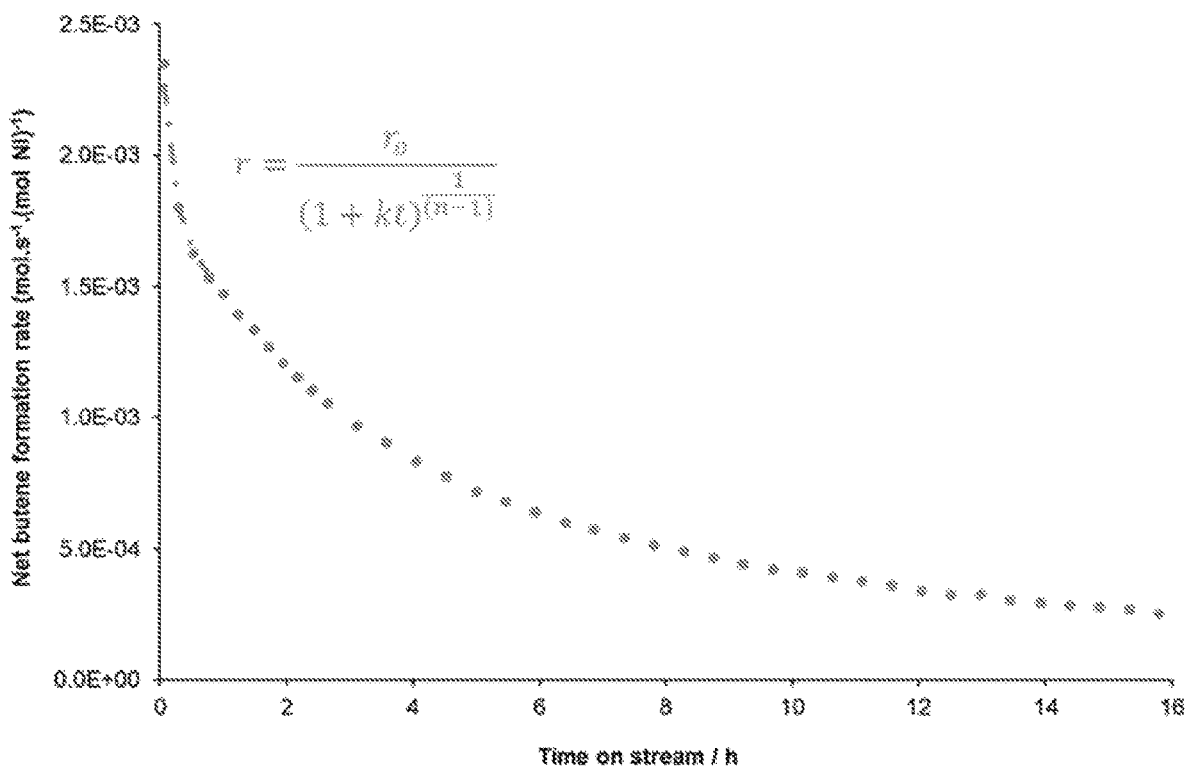

Effect of space time on initial net butene formation rate on Ni-Li-[Al]BEA at 453 K and ethene pressures: 0.3, 0.4, 0.6, 0.75 and 1 kPa.

Effect of space time on initial net butene formation rate on Ni-Li-[Al]BEA at 453 K and ethene pressures: 0.05, 0.1 and 0.2 kPa.

Net butene formation rate for H-[Al]BEA at 453 K, 0.2 kPa ethene and 0.008 mol ethene (mol $H^+)^{-1}$ $s^{-1}$ is fitted with an exponential deactivation model. $r_0$ is the initial net butene formation rate, $k_d$ is the apparent first order deactivation rate constant and t is time in hours.

Effect of space time on initial net butene formation rate for H-[Al]BEA at 453 K and 0.2 kPa ethene pressure.

Effect of space time on initial net butene formation rate on Ni-Li-[Zn]BEA at 453 K and ethene pressures - 0.2, 0.4, 0.6 and 0.7 kPa Dependence of initial ethene dimerization rate at 453 K on Ni-Li-[Al]BEA (■) and Ni-Li-[Zn]BEA (●) on the ethene pressure.

NICKEL-BASED MICROPOROUS AND MESOPOROUS CATALYSTS FOR SELECTIVE OLEFIN OLIGOMERIZATION

BACKGROUND

The present disclosure is directed to new catalyst compositions for the oligomerization of light alkenes, commonly known as olefins, especially gaseous alkenes, e.g., ethene, to longer chain olefin derivatives. The longer chain olefin derivatives have a high value as precursors to fuels, chemicals and lubricants.

Recent developments in hydraulic fracturing and horizontal drilling technologies and the discovery of shale gas reserves in US has led to a rapid increase in production of natural gas and associated NGLs natural gas liquids (NGLs) such as ethane, propane and butane. Shale gas has become an increasingly important source of natural gas in the United States, and the U.S. government's Energy Information Administration predicts that by 2035, forty to fifty percent of the United States' natural gas supply will come from shale gas. More efficient utilization of petroleum and gas reserves is an important strategy for the deployment of future energy generation. The transformation of shale gas to transportation fuels, chemicals and lubricants is one of the strategies to utilize the shale gas reserves to their highest value. These transformation technologies can be used to upgrade hydrocarbons from traditional, non-shale sources, as well.

Current state-of-the art olefin production includes thermal cracking of alkanes at high temperatures, such as via steam cracking processes. For hydrocarbons with three or more carbons, thermal cracking results in mixtures of C—C and C—H cracked products, resulting in a mix of products that include propene, ethene, aromatics, butenes, hydrogen, and methane. The resulting products must then be separated cryogenically at great cost. Over the past decade, the US petrochemical industry has been gradually shifting its feedstock for steam cracking from naphtha to ethane and also many new ethane cracker projects are in the process of being built. Using ethane as a feedstock for steam cracking produces abundant amounts of ethene (typically about 75% of cracker output) and as a result, the ethene production capacity of the US is projected to increase substantially relative to its current capacity. On the other hand, using ethane as feedstock for steam cracking produces less of the heavier co-products such as propene, butenes and aromatics (benzene, toluene, and xylene which together can be referred to as BTX), when compared to the co-products formed using naphtha as a feedstock for steam cracking. Given the abundant availability of ethene, an opportunity exists to devise alternative pathways to produce these deficit co-products, as well as other heavier olefins, starting from ethene as a reactant.

Zeolites, molecular sieves, and related microporous and mesoporous materials have the ability to control the access of reactants and products based on their size and shape to catalytically active sites within the pores of these materials. Thus, they can preferentially contain only those transition states which can be stabilized while excluding others. These phenomena have been described as concepts of shape selectivity and size exclusion and are considered to be a hallmark of zeolite catalysis. However, it has been shown that a zeolite framework of oxygen atoms can stabilize confined reactants and transition states by van der Waals forces. Thus, these van der Waals forces influence the catalytic rates and selectivity. This imparts additional catalytic diversity to porous materials beyond size exclusion.

For example, Gounder and Iglesia [Catalytic Alkylation Routes via Carbonium-Ion-Like Transition States on Acidic Zeolites, ChemCatChem, 3 (2011) 1134-1138] have shown that the ethene dimerization rates on Brønsted acid sites at 748 K, when measured under dilute H$^+$ site coverages, exhibit a second-order dependence on ethene pressure, and the rate constants vary for different zeolite frameworks such as FER, MOR and MFI. The second-order ethene dimerization rate constants reflect the stability of confined dimerization transition states relative to that of two unconfined gas-phase ethene molecules and these transition states are preferentially stabilized by confinement relative to the unconfined gas-phase ethene molecules. Alkene oligomerization reactions on Brønsted acid sites, however, are non-selective as these sites also lead to isomerization, alkylation and cracking reactions.

On the other hand, these reactions have been reported to occur with high selectivity for nickel cations supported on silica, silica-alumina, zeolites and mesoporous materials. There still exits a debate on the nature of the active site for ethene dimerization and further investigation is needed. Although several reports indicate that Ni$^{2+}$ are active sites for dimerization of alkenes, these sites are often present in many different surrounding environments, different metal structures and in the presence of other active sites. In summary, the varied distribution of Ni cations, the presence of other active sites and metal structures make it difficult to study the effect of a Ni$^{2+}$ surrounding environment and there are contrasting reports on the effect of pore size variation for alkene dimerization.

There is a need to understand the independent effect of these structural properties on the kinetics of alkene dimerization and oligomerization. There is a further need for improved catalysts for use in alkene dimerization and oligomerization reactions.

BRIEF DESCRIPTION OF THE DRAWINGS

The accompanying drawings are incorporated into and form a part of the specification to illustrate aspects and examples of the present disclosure. These figures together with the description serve to explain the general principles of the disclosure. The figures are only for the purpose of illustrating examples of how the various aspects of the disclosure can be made and used and are not to be construed as limiting the disclosure to only the illustrated and described examples.

FIG. 10 is graphs of (A) Ethene conversion for oxidatively pretreated Ni—Li—[Zn]BEA, H—[Al]BEA, Ni—Li—[Al]BEA and Ni—H—[Al]BEA. (B) Ethene for non-pretreated Ni—Li—[Al]BEA and $NH_3$ poisoned Ni—Li—[Al]BEA.

FIG. 13 is a graph of transient 2-butenes/1-butene and isobutene/1-butene ratios for H—[Al]BEA and Ni—Li—[Al]BEA and transient 2-butenes/1-butene ratio for Ni—Li—[Zn]BEA.

FIG. 16 are graphs of (A) Transient net butene formation rate for Ni—Li—[Al]BEA and Ni—Li—[Zn]BEA. (B) Dependence of the duration of activation period on ethene partial pressure for Ni—Li—[Al]BEA and Ni—Li—[Zn]BEA.

FIG. 20 is a graph of the hyperbolic deactivation model fitted to the initial transient of the net butene formation rate measured on Ni—Li—[Al]BEA.

DETAILED DESCRIPTION

Figure 1:
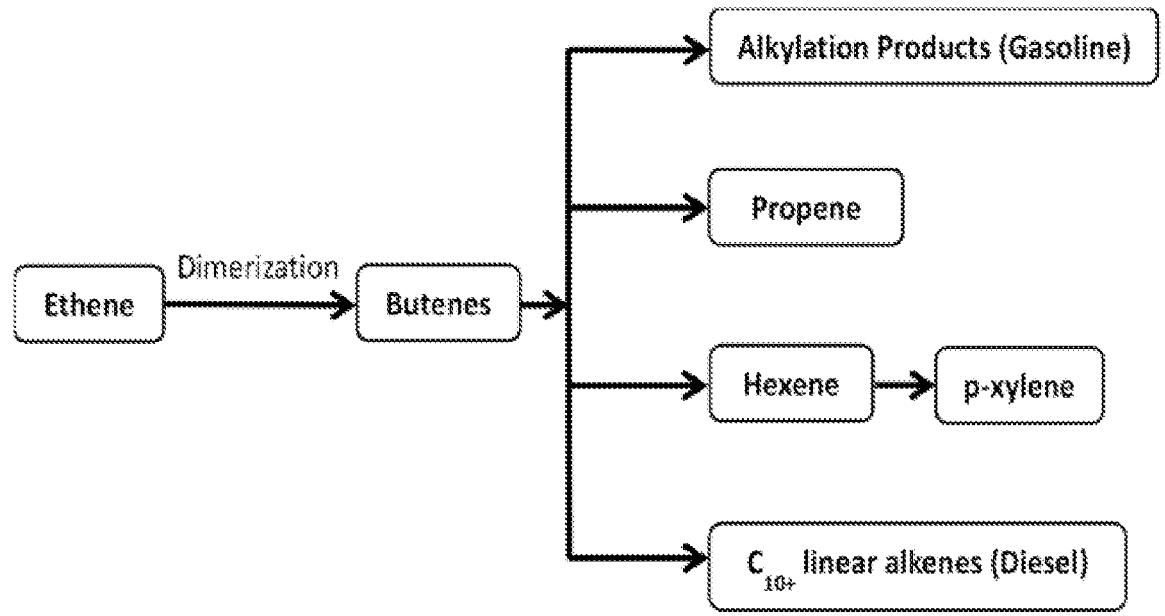
FIG. 1 is a simplified block flow diagram illustrating how ethene oligomerization forms an entry step chemistry to form higher molecular weight compounds.

The following detailed description illustrates embodiments of the present disclosure. These embodiments are described in sufficient detail to enable a person of ordinary skill in the art to practice these embodiments without undue experimentation. It should be understood, however, that the embodiments and examples described herein are given by way of illustration only, and not by way of limitation. Various substitutions, modifications, additions, and rearrangements may be made that remain potential applications of the disclosed techniques. Therefore, the description that follows is not to be taken as limiting on the scope of the appended claims. In particular, an element associated with a particular embodiment should not be limited to association with that particular embodiment but should be assumed to be capable of association with any embodiment discussed herein.

Definitions

For the purpose of this description and appended claims, the following terms are defined.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All processes described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The term "alkane" or "paraffin" means substantially saturated compounds containing hydrogen and carbon only, e.g., those containing <1% (molar basis) of unsaturated carbon atoms. The term alkane encompasses $C_1$ to $C_6$ linear, iso, and cyclo alkanes.

As used herein, an "alkene" or "olefin" refers to any unsaturated hydrocarbon containing one or more pairs of carbon atoms linked by a double bond. The olefins described herein include cyclic or aliphatic olefins, and include mono-olefins, di-olefins, tri-olefins, etc.

The term "$C_n$" hydrocarbon wherein n is a positive integer, e.g., 1, 2, 3, 4, or 5, means hydrocarbon having n carbon atom(s) per molecule. The term "$C_{n+}$" hydrocarbon wherein n is a positive integer, e.g., 1, 2, 3, 4, or 5, means hydrocarbon having at least n carbon atom(s) per molecule. The term "$C_{n-}$" hydrocarbon wherein n is a positive integer, e.g., 1, 2, 3, 4, or 5, means hydrocarbon having no more than n number of carbon atom(s) per molecule.

As used herein, a "catalyst" is any substance or material which changes the rate of conversion of alkanes to alkenes but is not, itself, consumed.

The terms "comprise," "comprises," "comprising," "include," "includes," "including," "have," "haves," and "having" are interchangeable and not intended to be limiting.

The term "hydrocarbon" means compounds containing hydrogen bound to carbon, and encompasses (i) saturated hydrocarbon, (ii) unsaturated hydrocarbon, and (iii) mixtures of hydrocarbons, including mixtures of hydrocarbons (saturated and/or unsaturated) having different values of n.

The term "zeolite" means microporous minerals commonly used as commercial adsorbents and catalysts.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The present disclosure relates generally to oligomerization reactions of light olefins. More particularly, the present disclosure relates to catalysts which can enable oligomerization of light olefins to longer chain olefin derivatives. Embodiments of the present disclosure provide a method to produce such catalysts.

The present disclosure is directed to novel catalyst compositions and their respective use in the oligomerization reactions of light olefins. In an embodiment the catalyst comprises nickel supported on a crystalline silica-based molecular sieve oxide. The catalyst is an active and selective catalyst for the catalytic oligomerization reactions of light olefins.

The oligomerization of light olefins (alkene molecules having from 2 to 6 carbon atoms) is an important industrial reaction and represents a route to the production of intermediates used for the production of motor fuels, plasticizers, pharmaceuticals, dyes, resins, detergents, lubricants and additives. The oligomerization of light olefins, such as ethene and propene, represents an important industrial route to the production of environmentally friendly synthetic liquid products, free of sulfur and aromatics. Thus, ethene oligomerization forms an entry step chemistry to form higher molecular weight compounds, which is shown in the block flow diagram of FIG. 1.

Methods and Materials

Nickel (Ni) is the fourth most abundant transitional metal on earth. It is of low cost and of lower toxicity compared with many catalysts industrially used. Ni has been extensively used in reforming and selective hydrogenation reactions. The present disclosure includes new Ni catalysts for alkene oligomerization that yields high stability and selectivity. The new Ni catalysts are reproducible and robust for the oligomerization of light alkenes to larger olefins.

The catalysts of the present disclosure can be prepared by impregnating a support material with a Group VIII metal selected from the group consisting of nickel, iron, cobalt, and combinations thereof, to form a precursor. The precursor can then be dried and calcined. The amount of the Group VIII metal to be impregnated can range from about 0.001 wt % to about 25 wt %, optionally about 0.01 wt % to about 10 wt %, optionally from about 1.0 wt % to about 5 wt % calculated on an elemental basis of the final catalyst composition.

The impregnations can be accomplished via an incipient wetness technique; however, other suitable techniques known to those skilled in the art are also suitable. An absorption technique from a dilute or concentrated solution, with subsequent filtration or evaporation to effect uptake of the metallic component, may also be used. Frequently, the pH of the solution will be adjusted to provide for optimum intercalation. In an embodiment the pH can be limited to between 8-14, optionally between 9-13, optionally between 10-12, optionally between 10.5-11.5, optionally the pH can be held at 11 throughout the impregnation procedure. Contacting time can be anywhere from at least about 1 minute to about 1 month, optionally about 1 minute to 1 week, optionally, about 1 to about 24 hours. In some instances, the higher the contacting temperature the shorter the contacting time that is necessary. Such contacting times can be readily determinable by one skilled in the art. The resulting material can then be separated by any conventional means, washed and dried. The impregnated support can then be dried followed by calcination and reduction.

The drying can be conducted at ambient temperature at first, such as for about 3 hours, followed by an elevated temperature, such as about 125° C. for about 8 hours. The calcination can be conducted at increasingly elevated temperature, such as at a temperature from 200° C. to 650° C., in the presence of oxygen, or in an air stream, or in the presence of a mixture of oxygen and an inert gas. In an example, the calcination can be about 200° C. for 30 minutes, and then 550° C. for 30 minutes or longer. The calcination process can be a staged calcination, wherein the temperatures are changed throughout the process. The temperature changes need not be a linear increase, but can be increased for example from 200° C. to 400° C. and held at 400° C. followed by another increase, etc. However, linear increases in temperature can also be used. This calcination can be conducted for periods ranging from about 30 minutes to 24 hours in either flowing or static gases. After calcination, the catalyst can be reduced in flowing hydrogen, or a hydrogen containing inert gas stream, at increasingly elevated temperatures, such as at 200° C. for 30 minutes and then at 550° C. for 30 minutes. The times, temperatures and rates of change during the drying, calcination and reducing process of the impregnated support are variable, can be readily determinable by one skilled in the art, and is not to be a limitation upon the present disclosure.

The metals can be added in any suitable manner known in the art, such as non-limiting examples of: supported on a substrate or an inert support, added to a binder, placed on or within a zeolite or other catalyst support, such as by ion exchange, incipient wetness impregnation, pore volume impregnation, soaking, percolation, wash coat, precipitation, and gel formation.

The various elements that make up the components for the catalyst can be derived from any suitable source, such as in their elemental form, or in compounds or coordination complexes of an organic or inorganic nature, such as carbonates, oxides, hydroxides, nitrates, acetates, chlorides, phosphates, sulfides and sulfonates. The elements and/or compounds can be prepared by any suitable method known in the art for the preparation of such materials.

The term "support" or "substrate" as used herein is not meant to indicate that this component is necessarily inactive, while the other metals and/or promoters are the active species. On the contrary, the support or substrate can be an active part of the catalyst. The term substrate would merely imply that the substrate makes up a significant quantity, generally 10% or more by weight, of the entire catalyst. The active metals individually can typically range from 0.001% to 60% by weight of the catalyst, optionally from 0.01% to 50%. If more than one active metal is combined, they together generally can range from 0.01% up to 70% by weight of the catalyst.

The supports of the present disclosure can be any suitable support, such as for non-limiting examples: silica, silicon dioxide, titanium dioxide, silica pillared clays, metal modified silica, metal oxide modified silica, silica-pillared clays, metal oxide modified silica-pillared clays, silica-pillared micas, metal oxide modified silica-pillared micas, silica-pillared tetrasilicic mica, silica-pillared taeniolite, and combinations thereof. Such supports are commercially obtainable or prepared by techniques known to those skilled in the art.

Prior art also describes the use of metal-containing zeolite catalysts, in which the metal is incorporated into the zeolite structure by some process, such as ion exchange or impregnation. However, swings in catalytic activity may occur in the case of a metal impregnated catalyst as metal can be lost from the pore structure of a zeolite or molecular sieve type substrate. Another drawback is the high probability of plugging of pores with coke when the metal is incorporated into a zeolite or molecular sieve type structure.

In one embodiment, the catalyst can be prepared by combining a substrate with the active metal elements. Embodiments of a substrate can be a molecular sieve, from either natural or synthetic sources. Zeolites can be an effective substrate, can be commercially available, and are well known in the art. Alternate molecular sieves also contemplated are zeolite-like materials such as for example crystalline silicoaluminophosphates (SAPO) and the aluminophosphates (ALPO).

Microporous and mesoporous Zn-containing molecular sieves are suitable for the present disclosure and all are within the scope of the catalyst preparation and usage discussed herein. Numerous Zn-containing molecular sieves are possible for use whose preparation routes are known. These zincosilicate structures may be promising olefin oligomerization catalysts if Ni were exchanged onto them. Non-limiting listings are contained in Tables 1 and 2 summarizing their salient properties.

components in effective amounts. According to an embodiment the substrate is charged with active metal via an incipient wetness impregnation. Other impregnation techniques such as by soaking, pore volume impregnation, or percolation can optionally be used. Alternate methods such as ion exchange, wash coat, precipitation, and gel formation can also be used.

When slurries, precipitates or the like are prepared, they will generally be dried, usually at a temperature sufficient to volatilize the water or other carrier, such as from 100° C. to 250° C., with or without vacuum. Irrespective of how the components are combined and irrespective of the source of the components, the dried composition can be calcined in the presence of a free oxygen-containing gas, usually at temperatures between about 300° C. and about 900° C. for from 1 to 24 hours. The calcination can be in an oxygen-containing atmosphere, or alternately in a reducing or inert atmosphere.

Binder material, extrusion aids or other additives can be added to the catalyst composition or the final catalyst composition can be added to a structured material that provides a support structure. For example, the catalyst component and/or the composite catalyst can include an alumina or aluminate framework as a support. Upon calcination these elements can be altered, such as through oxidation which would increase the relative content of oxygen within the final catalyst structure. The combination of the composite catalyst of the present invention combined with additional elements such as a binder, extrusion aid, struc-

TABLE 1

Zincosilicate Structures.

| Material | Framework type | Channels | LCD[a] (nm) | PLD[b] (nm) | LCD/PLD | Pore interconnectivity | Ref. |
|---|---|---|---|---|---|---|---|
| CIT-6 | BEA* | 12-MR | 0.69 | 0.67 | 1.03 | 3-D | [90] |
| VPI-8 | VET | 12-MR | 0.66 | 0.66 | 1.00 | 1-D | [91-92] |
| Zn-MFI | MFI | 10-MR | 0.70 | 0.50 | 1.40 | 3-D | [93-95] |
| Zn-MOR | MOR | 12-MR, 8-MR | 0.65 | 0.65 | 1.00 | 1-D | [96] |
| Zn-MCM-41 | n.d. | n.d. | n.d. | n.d. | n.d. | 1-D | [97-99] |
| Zn-MCM-48 | n.d. | n.d. | n.d. | n.d. | n.d. | 3-D | [100] |

[a]LCD: Largest Cavity Diameter.
[b]PLD: Pore Limiting Diameter.
n.d.: not defined (for mesoporous materials).

TABLE 2

Other Zincosilicate Structures.

| Material | Framework type | Channels | LCD[a] (nm) | PLD[b] (nm) | LCD/PLD | Pore interconnectivity | Ref. |
|---|---|---|---|---|---|---|---|
| VPI-7 | VSV | 8-MR, 9-MR | 0.50 | 0.34 | 1.47 | 3-D | [101-102] |
| VPI-9 | VNI | 8-MR | 0.54 | 0.32 | 1.69 | 3-D | [103] |
| RUB-17 | RSN | 8-MR, 9-MR | 0.58 | 0.34 | 1.71 | 3-D | [104] |

[a]LCD: Largest Cavity Diameter.
[b]PLD: Pore Limiting Diameter.
n.d.: not defined (for mesoporous materials).

The present disclosure is not limited by the method of catalyst preparation, and all suitable methods should be considered to fall within the scope herein. Conventional methods include co-precipitation from an aqueous, an organic, or a combination solution-dispersion, impregnation, dry mixing, wet mixing or the like, alone or in various combinations. In general, any method can be used which provides compositions of matter containing the prescribed tured material, or other additives, and their respective calcination products, are included within the scope of the invention.

The prepared catalyst can be ground, pressed, sieved, shaped and/or otherwise processed into a form suitable for loading into a reactor. The reactor can be any type known in the art, such as a fixed bed, fluidized bed, or swing bed reactor. Optionally an inert material, such as quartz chips, can be used to support the catalyst bed and to locate the catalyst within the bed. Depending on the catalyst, a pretreatment of the catalyst may, or may not, be necessary. In an embodiment, for the pretreatment, the reactor can be heated to elevated temperatures, such as 200° C. to 900° C. with an air flow, such as 100 mL/min, and held at these conditions for a length of time, such as 1 to 3 hours. Then, the reactor can be brought to the operating temperature of the reactor, for example 150° C. to 600° C., or optionally down to atmospheric or other desired temperature. The reactor can be kept under an inert purge, such as under a nitrogen or helium purge.

The catalyst of the present disclosure can be contacted with a feedstream containing $C_2$ to $C_5+$ alkenes under oligomerization conditions, for a time and at a temperature sufficient to produce longer olefins. The alkenes may be co-fed with a stream of $H_2$ and/or inert gas. In an embodiment, the $H_2$:alkene or inert:alkene ratio can range from about 0.1 to 5, optionally 0.1 to 1.0. Steam may also be co-fed if desired as a diluent or as a heat transfer agent.

In an embodiment the catalyst of the present disclosure can undergo in-situ regeneration, which can lower operating costs by decreasing the amount of time the reactor must be offline. The regeneration can be done by hydrogen and water vapor stripping at the reaction temperature. In an embodiment the catalyst of the present disclosure can undergo ex-situ regeneration.

In another embodiment, the present disclosure is a process for the oligomerization of alkenes to larger olefins. The process includes the steps of introducing an alkene feedstock into a reaction chamber, passing the feedstock over a oligomerization catalyst at reaction conditions effective to provide a product containing olefin hydrocarbons, and regenerating the catalyst in-situ, when necessary.

The alkene feedstock can be alkenes containing less than 10 carbon atoms. The feedstock can consist primarily of $C_2$-$C_6$ alkenes. The alkene feedstock can be obtained from any suitable source. Co-feed can contain hydrogen, or water vapor. In an illustrative embodiment the alkene feed can contain primarily ethene. In an illustrative embodiment the alkene feed can contain primarily propene. In an illustrative embodiment the alkene feed can contain primarily butene. In an illustrative embodiment the alkene feed can contain primarily ethene and propene. In an illustrative embodiment the alkene feed can contain primarily propene and butene. In an illustrative embodiment the alkene feed can contain primarily butene and pentene. In an illustrative embodiment the alkene feed can contain primarily $C_3$-$C_6$ alkenes. In an illustrative embodiment the alkene feed can contain primarily $C_4$-$C_6$ alkenes.

The reaction chamber can house any suitable catalyst system, such as a fixed catalyst bed, a moving bed or a fluidized bed. Single or multiple catalyst beds can be used, and the reactor can be a swing reactor.

In embodiments the reaction can take place at a temperature of from 50° C. to 350° C., optionally from 120° C. to 200° C., optionally from 250° C. to 350° C. The pressure can be in the range of from 0.5 psig to 600 psig, optionally from 5 psig to 50 psig, optionally from 350 psig to 600 psig. The weight hourly space velocity can be from 0.5 to 600 $hr^{-1}$, optionally from 10 to 200 $hr^{-1}$, and optionally from 300 to 550 $hr^{-1}$.

The reaction products can be processed and separated by cooling or other standard recovery or separation techniques.

The following examples are given to provide a better understanding of the present invention and are not intended to limit the scope of the invention in any way.

Experimental Data

It is evident that the $Ni^{2+}$ active site itself, residual $H^+$ sites, and the surrounding pore structure are the main structural properties that influence the dimerization and oligomerization chemistry of alkenes. There is a need to understand the independent effect of these structural properties on the kinetics of alkene dimerization and oligomerization. Thus, catalytic materials with isolated $Ni^{2+}$ sites within different pore environments and in the absence of any other active sites or metal structures were prepared to unambiguously probe the reactivity of isolated $Ni^{2+}$ sites within its known surrounding environments. It is believed that the elements iron and cobalt that are similar to nickel may behave in similar manner, therefore the present disclosure is not to be limited to nickel only and that nickel, iron, cobalt, and combinations thereof may be used in respect to the disclosure herein.

Figure 2:
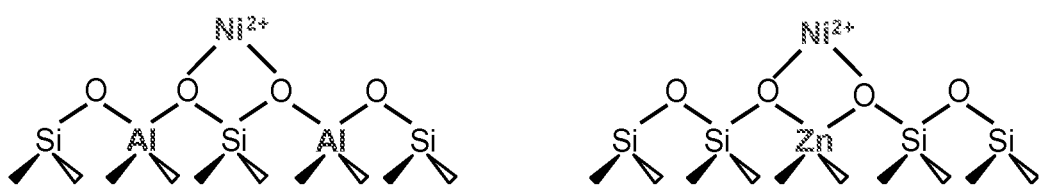
FIG. 2 is an illustration of the structure of an extra framework Ni$^{2+}$ coordinated with two framework Al$^{3+}$ centers in a paired configuration (left; aluminosilicate) and with one framework Zn$^{2+}$ center (right; zincosilicate).

The prepared catalysts with Ni active site structures were based on aluminosilicate and zincosilicate supports as shown in FIG. 2. The exchange of one extra framework $Ni^{2+}$ site requires two framework $Al^{3+}$ centers in a paired configuration as shown in the aluminosilicate structure or one framework $Zn^{2+}$ center as shown in the zincosilicate structure.

Zincosilicate supports were used which enable the isolation of $Ni^{2+}$ centers within porous solids. Zincosilicate supports contain isolated divalent framework charges ($Zn^{2+}$) which can be selectively charge compensated by $Ni^{2+}$ cations, thus leaving no residual $H^+$ or alkali cations or alkaline earth cation sites. Zincosilicate support compositions (Ni—H-CIT-6 and Ni—Zn-MCM-41) have been recently tested for propene oligomerization at 453K (180° C.) [M. A. Deimund, J. Labinger, M. E. Davis, Nickel-Exchanged Zincosilicate Catalysts for the Oligomerization of Propylene, ACS Catal., 4 (2014) 4189-4195]. The isolation of $Ni^{2+}$ using zincosilicate supports will help to study the exclusive effect of $Ni^{2+}$ sites and its surrounding environment on rates and selectivity of alkene dimerization.

Nickel Exchanged Zn-Beta

Zincosilicate material CIT-6 was synthesized in its Li form. Li-CIT-6 was prepared by adding 0.99 g of zinc acetate dihydrate (Sigma Aldrich, 99.9% pure) and 0.316 g of lithium hydroxide monohydrate (Sigma Aldrich, 99.95% pure) to 46.73 g of water and 22.87 g of tetraethylammonium hydroxide (Sigma Aldrich, 40% (w/w)). The mixture was stirred for about 0.25 hours until all the solids were completely dissolved. The mixture was then added with 22.87 g of colloidal silica (Sigma Aldrich, 40% (w/w)) and it was further stirred for 2 hours. The final reaction mixture gel had the following molar composition: 0.65 TEAOH/$SiO_2$/0.05 $LiOH.H_2O$/0.03 $Zn(CH_3COO)2.2H_2O$/30 $H_2O$. The gel was then transferred to Teflon-lined, stainless steel autoclaves and was heated statically at 413K (140° C.) for 138 hours in a forced convection oven. The product was collected by centrifugation and was washed with purified water and acetone. It was then dried overnight in a drying oven at 363K (90° C.).

The as-made Li-CIT-6 catalysts were exchanged with nickel using a template ion exchange procedure [33]. Nickel exchange was carried out at 348K (75° C.) for 5 hours using 100 mL of aqueous 0.1 M $Ni(NO_3)_2$ (Sigma Aldrich, 99.999%) solution per 1 g of solid catalyst. The pH of the exchange solution was adjusted to 7 at the start using 0.1 N NaOH (Sigma Aldrich, 99.99%). The exchanged product was collected by centrifugation and washed with water. The washed catalyst was dried at ambient temperature within a centrifuge tube by blowing a small stream of compressed air over it. The organic template and the residual nitrates were removed by treatment in flowing dry air (20 cm$^3$ s$^{-1}$ gcat$^{-1}$, 99.999% UHP, Matheson Tri-Gas) at 853K (580° C.) at 0.0167° C. s$^{-1}$ for 10 hours inside a muffle furnace.

Nickel Exchanged Al-Beta

NH$_4$-Beta (CP814E Lot #2493-65) catalyst with Si/Al=12 was obtained from Zeolyst International. The NH$_4$-form Al-Beta catalyst was converted to its H-form form by treatment in flowing dry air (1.67 cm$^3$ s$^{-1}$ gcat$^{-1}$, 99.999% UHP, Matheson Tri-Gas) at 773K (500° C.) at 0.0167° C. s$^{-1}$ for 4 hours. It was exchanged with nickel at ambient temperature for 16 hours using 100 mL of aqueous 0.3 M Ni(NO$_3$)$_2$ (Sigma Aldrich, 99.999%) solution per 1 g of solid catalyst. The pH of the solution was maintained at 7 during the first 4 hours of exchange using 0.1 N NaOH (Sigma Aldrich, 99.99%). The product was collected by centrifugation and was washed with purified water. The washed catalyst was dried at ambient temperature within a centrifuge tube by blowing a small stream of compressed air over it. The residual nitrates were removed by treatment in flowing dry air (20 cm$^3$ s$^{-1}$ gcat$^{-1}$, 99.999% UHP, Matheson Tri-Gas) at 773K (500° C.) at 0.0167° C. s$^{-1}$ for 4 hours.

The nickel exchanged Na-Beta was synthesized by simultaneous aqueous phase ion-exchange of commercially obtained NH$_4$-Beta with Na$^+$ and Ni$^{2+}$ ions. The procedure followed was the same as above except that 3 g of NH$_4$-Beta was added to an aqueous mixture of 250 mL 1 M NaNO$_3$ (Sigma Aldrich, 99.0%) solution and 50 mL 0.3 M Ni(NO$_3$)$_2$ (Sigma Aldrich, 99.999%) solution.

Catalyst Characterization

The crystal morphology of the catalysts was determined by powder X-ray diffraction patterns (XRD) collected using Rigaku SmartLab X-ray diffractometer and Cu Kα radiation. Scanning Electron Microscope (SEM) images were captured using FEI NOVA nanoSEM FESEM (Purdue Life Science microscopy facility) at high tension voltage of 10.0 kV. Nitrogen adsorption isotherms were measured using Micromeritics ASAP 2000 at normal boiling point of nitrogen. The thermogravimetric and heat flow analysis was done using TA Instruments SDT Q600 with an air flow of 4000 cm$^3$ s$^{-1}$ g$^{-1}$ and temperature ramp of 10° C. min$^{-1}$ from 303K (30° C.) to 1173K (900° C.). The elemental composition of the catalysts was determined by atomic absorption spectroscopy (AAS) using Perkin Elmer AAnalyst 300.

Catalytic Rate Measurements

Ethene dimerization rates were measured in a plug-flow tubular quartz reactor under differential conditions (<0.5% conversion). Before rate measurements, catalysts (0.01-0.10 g) were treated at 806K (555° C.) at 0.0167° C. s$^{-1}$ in a 5% O$_2$/95% He mixture (16.7 cm$^3$ gcat$^{-1}$ s$^{-1}$, 99.999%, Matheson Tri-Gas) for 4 hours and then in pure He flow (16.7 cm$^3$ gcat$^{-1}$ s$^{-1}$, 99.999%, Matheson Tri-Gas) for 2 hours while ethene reactant mixture (1% C$_2$H$_4$, 5% Ar, 94% He, Matheson Tri-Gas, 99.999% purity) was transferred to GCMS system (Agilent 7890B GC; Agilent 5975C MSD) via heated lines (393K) (120° C.) for calibration purposes. Reactants and products were separated using GS-AL/KCl capillary (0.530 mm ID×50 m; Agilent) column and detected using flame ionization detector. The products were identified using the NIST spectra library database and also verified by injecting known hydrocarbon standards. Reactants were diluted with He (99.999%, Matheson Tri-Gas) to vary the partial pressure and molar rates of C$_2$H$_4$ (0.01-1 kPa; 10$^{-7}$-10$^{-4}$ (mol C$_2$H$_4$) g$^{-1}$ s$^{-1}$). Rate constants measured between 453K (180° C.) and 513K (240° C.) were used to estimate activation energies and pre-exponential factors. For loading small quantities of active catalysts, the active catalysts were premixed with pure-silica Beta (Si-BEA-F), which was independently determined to be an inert material for ethene dimerization under the tested experimental conditions. The catalysts were regenerated in between two consecutive experiments, because they were observed to deactivate with time on stream and thus, each experiment was started with a fresh and active catalyst. The molar butene selectivity is calculated as the ratio of net molar flow rate of butenes to the molar flow rate of all the products formed and detected. The ethene conversion is determined as the ratio of total carbon molar flow in products formed to the total carbon molar flow in ethene feed.

Figure 3:
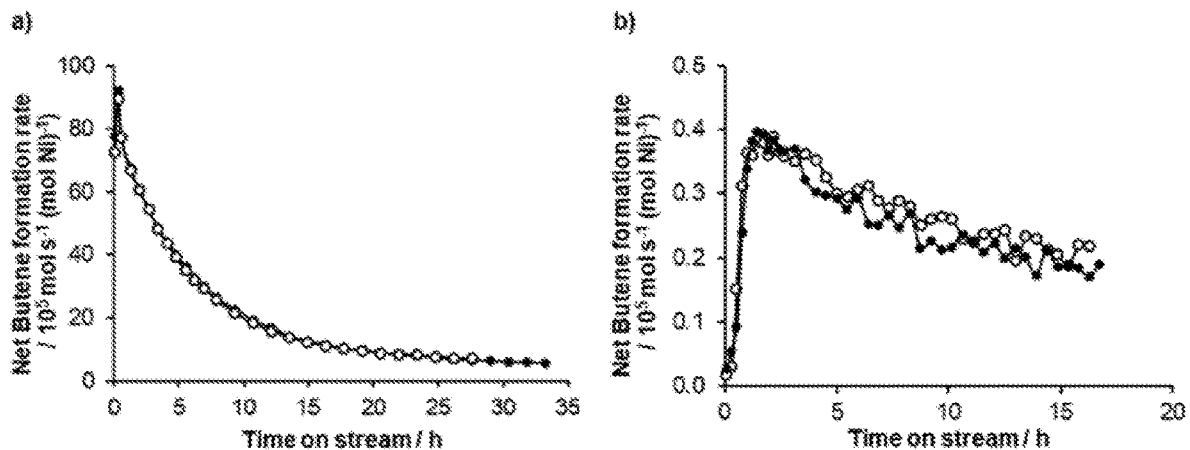
FIG. 3 is a graph of net butene formation rate vs. time-on-stream for Ni—Li—[Al]BEA and Ni—Li—[Zn]BEA catalysts under ethene dimerization.

To determine the regeneration capability of Ni—Li—[Al] BEA and Ni—Li—[Zn]BEA, fresh catalyst samples were loaded into the reactor and tested at 453K (180° C.) and 0.2 kPa ethene pressure. After the reaction run was complete, the catalysts were regenerated in 5% O2/He at 803K (530° C.) for 4 hours, before subjecting them again to the same reaction conditions. The time on stream behavior for net butene formation rate (453K (180° C.) and 0.2 kPa ethene) measured on the fresh and the regenerated samples of Ni—Li—[Al]BEA and Ni—Li—[Zn]BEA is shown in FIGS. 3 (a) and (b), respectively. The fresh and the regenerated samples exhibited substantially identical time on stream behavior for the net butene formation rate, for both Ni—Li—[Al]BEA and Ni—Li—[Zn]BEA. These results indicate that the used catalysts can be fully regenerated by treating them with 5% O2/He at 803K (530° C.) for 4 hours.

Nickel Site Characterization

Characterization of Synthesized Li—[Zn]BEA Material

Figure 4:
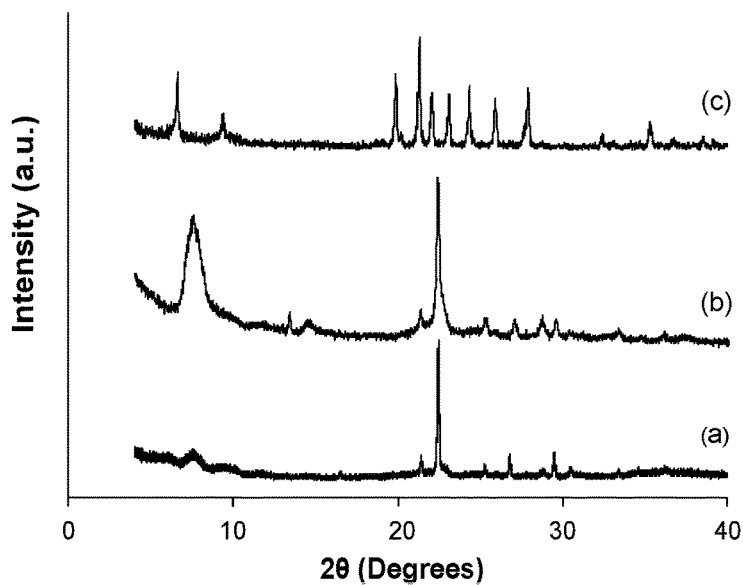
FIG. 4 is a graph of XRD patterns of (a) As-made Li—[Zn]BEA, (b) SDA free Li—[Zn]BEA and (c) As-made VPI-8 catalysts.
Figure 5:
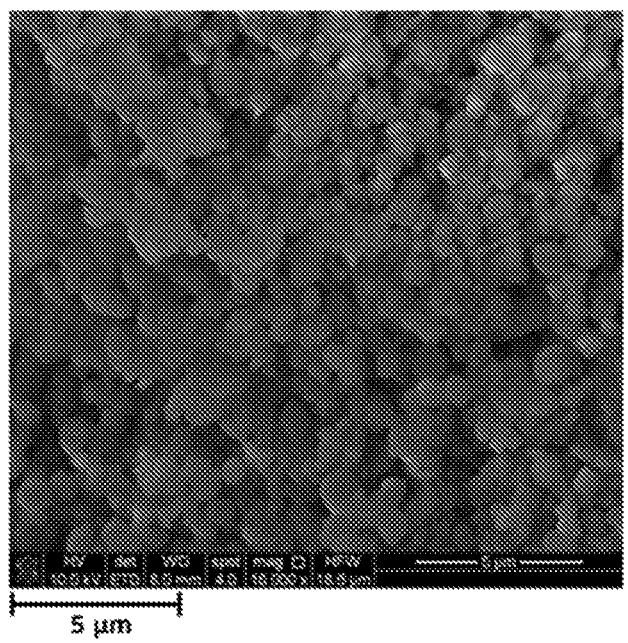
FIG. 5 is an SEM image for as-made Li—[Zn]BEA catalyst.

The powder XRD patterns for the as-made and SDA free form of Li—[Zn]BEA are shown in FIGS. 4 (a) and (b), respectively. The powder XRD patterns for this material are consistent with Beta framework topology and the slight differences observed between the as-made and SDA free Li—[Zn]BEA are because of high stacking fault densities present in Beta topology materials. The Li—[Zn]BEA crystals can further undergo a solid-state phase transformation to VPI-8 (VET framework), at long crystallization times. The powder XRD patterns as shown in FIGS. 4 (a) and (b) for Li—[Zn]BEA in this work, however, do not show any VPI-8 peaks FIG. 4 (c) at 2θ of 19.9°, 23°, 24.4°, 26°, 28° or 35.3°. Also, the SEM image FIG. 5 shows only pseudo-cubic or rounded shaped Li—[Zn]BEA crystals and only small traces of needle shaped VPI-8 crystals are observed, thus indicating miniscule or no presence of VPI-8 phase.

Figure 6:
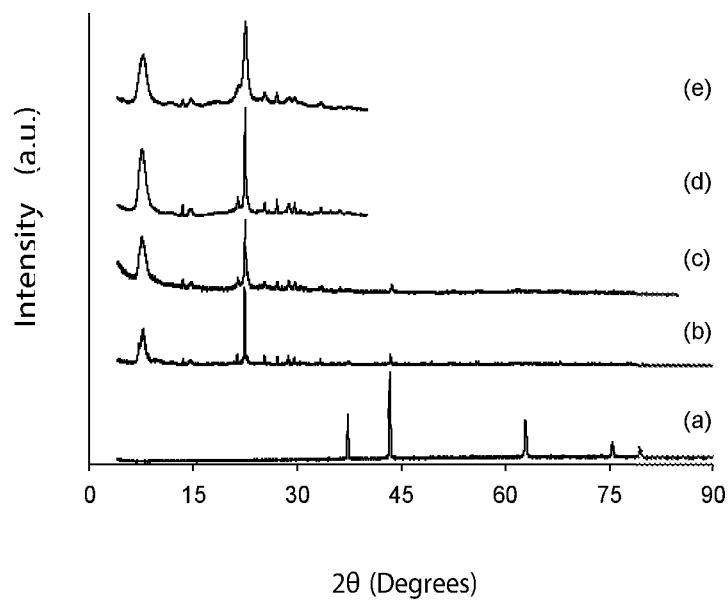
FIG. 6 is a graph of XRD patterns of (a) Bulk NiO, (b) NiO/Si-BEA, (c) SDA free Li—[Zn]BEA, (d) Ni—Li—[Zn]BEA, and (e) Ni—H—[Al]BEA.

Powder XRD patterns, as shown in FIG. 6, for Ni—Li—[Al]BEA, Ni—H—[Al]BEA, and Ni—Li—[Zn]BEA confirm a Beta framework topology and did not show diffraction peaks for bulk NiO at 2θ of 37.3°, 43.3°, 63°, 75.6° or 79.7°. Diffraction peaks for bulk NiO were also absent for the control material synthesized to contain NiO supported on Si-BEA (NiO/Si-BEA), indicating that any NiO nanoparticles on this material were small enough to be detected by X-ray diffraction.

Table 3 shows the Ar (87K) (−186° C.) micropore volumes for all the catalysts, which are also consistent with that of Beta topology, except that for Li—[Zn]BEA. The N2 (77K) (−196° C.) micropore volume of SDA free Li—[Zn] BEA was determined to be slightly lower around 0.16 cm$^3$ g$^{-1}$, which is attributed to the presence of extra framework Zn domains in this material. Elemental composition of all the catalysts was determined by atomic absorption spectroscopy and is shown in Table 3. The values of (2Ni+Li)/M (M denotes the framework heteroatom (Al or Zn)) for Ni—Li—[Al]BEA and Ni—Li—[Zn]BEA were similar to those of Li/M for the parent Li—[Al]BEA and Li—[Zn]BEA, respectively, indicating an ion-exchange stoichiometry of 2:1 for Li$^+$:Ni$^{2+}$ cations.

TABLE 3

Structural properties and elemental composition of catalysts.

| Catalyst | Ni (wt. %) | Si/[M] | Li/[M] | Ni/[M] | H$^+$/[M]$^a$ | Cation/[M] |
|---|---|---|---|---|---|---|
| H—[Al]Beta | — | 11.0 | 0 | 0 | 0.65 | 0.65 |
| Ni—H—[Al]Beta | 1.2 | 11.0 | 0 | 0.20 | 0.25 | 0.65 |
| Li—[Al]Beta | — | 11.0 | 1.01 | 0 | n.d. | 1.01 |
| Ni—Li—[Al]Beta | 1.7 | 11.0 | 0.50 | 0.26 | n.d. | 1.02 |
| Li—[Zn]Beta | — | 4.5 | 0.45 | 0 | n.d. | 0.45 |
| Ni—Li—[Zn]Beta | 1.3 | 4.5 | 0.08 | 0.16 | n.d. | 0.40 |

M denotes framework metal center (Al$^{3+}$ or Zn$^{2+}$)
n.m. denotes not measurable
$^a$measured by NH$_3$ TPD Synthesized aluminosilicate and zincosilicate materials of the MFI, BEA, and MCM-41 framework topologies were prepared as described in Table 4. These materials were exchanged partially with Ni$^{2+}$ cations that act as dimerization active sites, and contained either H$^+$ (which catalyze alkene side reactions) or Li$^+$ (which are catalytically inert) as the charge-balancing co-cations. Table 4 also summarizes representative kinetic data for ethene dimerization. It is found that the initial dimerization rates within each series of Ni-aluminosilicates or Ni-zincosilicates increase with pore diameter.

TABLE 4

Ni-zeolites synthesized, and initial ethene dimerization rates (453K (180° C.), 0.2 kPa C$_2$H$_4$).

| Catalyst | Pore Diameter (nm) | Si/M Ratio$^a$ | Ni/M Ratio$^a$ | Ni loading (wt. %) | Rate of C$_2$H$_4$ Dimerization (mol (mol Ni)$^{-1}$ s$^{-1}$) |
|---|---|---|---|---|---|
| Ni-H-[Al]BEA | 0.70 | 11.0 | 0.19 | 1.20 | 1.1 × 10$^{-3}$ |
| Ni-Li-[Al]MFI | 0.55 | 11.8 | 0.09 | 0.60 | 2.2 × 10$^{-4}$ |
| Ni-Li-[Al]MCM-41 | 2.6 | 11.6 | 0.29 | 2.25 | n.m.* |
| Ni-Li-[Al]BEA | 0.70 | 11.0 | 0.27 | 1.60 | 4.8 × 10$^{-4}$ |
| Ni-Li-[Zn]BEA | 0.70 | 4.5 | 0.16 | 1.80 | 3.5 × 10$^{-6}$ |
| Ni-Li-[Zn]MFI | 0.55 | n.m.* | n.m.* | n.m.* | n.m.* |
| Ni-Li-[Zn]MCM-41 | 2.6 | 22.0 | 0.20 | 0.75 | 9.1 × 10$^{-6}$ |

$^a$M denotes framework metal center (Al$^{3+}$ or Zn$^{2+}$)
*nm; not measured.

Figure 7:
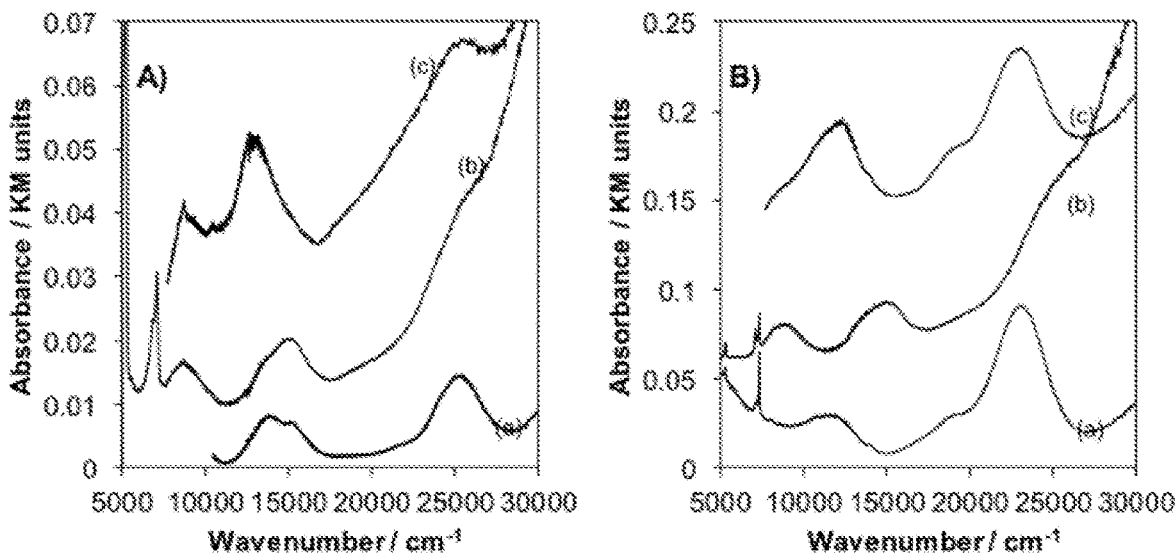
FIG. 7 are graphs of: (A) UV-vis spectra for (a) Ni—H—[Al]BEA, (b) Ni—Li—[Zn]BEA and (c) Ni—Li—[Al]BEA under hydrated conditions. (B) UV-vis spectra for (a) Ni—H—[Al]BEA, (b) Ni—Li—[Zn]BEA and (c) Ni—Li—[Al]BEA after dehydration.

Diffuse reflectance UV-visible (DRUV) spectroscopy was used to probe the coordination of Ni$^{2+}$ cations. FIGS. 7A and 7B show UV-vis spectra for Ni-exchanged catalysts in hydrated and dehydrated state, respectively. The Ni—Li—[Al]BEA catalyst in hydrated state showed absorption bands at 8600, 13200 and 25200 cm$^{-1}$, similar to those reported for Ni$^{2+}$ (H$_2$O)$_6$ (8500, 13500 and 25300 cm$^{-1}$) in the literature, and are assigned to the three spin-allowed d-d transitions $^3A_{2g}(F) \rightarrow {}^3T_{2g}(F)$, $^3A_{2g}(F) \rightarrow {}^3T_{1g}(F)$ and $^3A_{2g}(F) \rightarrow {}^3T_{1g}(P)$, for Ni$^{2+}$ in an octahedral coordination. Ni—Li—[Zn]BEA and Ni—H—[Al]BEA in hydrated state showed absorption bands at 8600, 13700, 15200 and 25200 cm$^{-1}$, consistent with previously published reports for Ni—H—[Al]BEA, Ni—H—[Al]Y and Ni—Na—[Al]Y. The absorption bands at 8600 and 25300 cm$^{-1}$ bands are also assigned to the transitions $^3A_{2g}(F) \rightarrow {}^3T_{2g}(F)$ and $^3A_{2g}(F) \rightarrow {}^3T_{1g}(P)$, respectively, while the doublet feature at 13700 and 15200 cm$^{-1}$ is assigned to the d-d transition $^3A_{2g}(F) \rightarrow {}^3T_{1g}(F)$. These observations suggest that under hydrated conditions, Ni$^{2+}$ cations on Ni—Li—[Al]BEA, Ni—Li—[Zn]BEA and Ni—H—[Al]BEA are present as octahedral Ni[(H$_2$O)$_6$]$^{2+}$ complexes.

Upon dehydration in an oxidative atmosphere, the absorption bands (FIG. 7B) for an octahedral Ni$^{2+}$ were retained for Ni—Li—[Zn]BEA, while these were not observed for Ni—H—[Al]BEA and Ni—Li—[Al]BEA. Ni—H—[Al]BEA and Ni—Li—[Al]BEA instead showed absorption bands at 5800, 12100, 18900 and 23000 cm$^{-1}$, consistent with previous published studies for Ni—H—[Al]BEA and for Ni$^{2+}$ grafted into framework of a dealuminated BEA. These absorption bands at 5800, 12100, 18900 and 23000 cm$^{-1}$ are assigned to the d-d transitions $^3T_1(F) \rightarrow {}^3T_2(F)$, $^3T_1(F) \rightarrow {}^3A_2(F)$ and $^3T_1(F) \rightarrow {}^3T_1(P)$ (doublet) respectively, for Ni$^{2+}$ in a pseudo-tetrahedral co-ordination. This doublet for the transition $^3T_1(F) \rightarrow {}^3T_1(P)$ is attributed to the splitting of this transition into its individual components caused by distortion of the tetrahedron, as observed for Ni$^{2+}$ cations on silica, A zeolite and Y zeolite. The sharp features at 5250 and 7200 cm$^{-1}$ are assigned to the combination of stretching and bending modes of H$_2$O, and the first overtone of silanol O—H stretching vibration, respectively. Thus, UV-vis spectroscopy for Ni—Li—[Al]BEA, Ni—H—[Al]BEA and Ni—Li—[Zn]BEA under hydrated and dehydrated conditions indicates that Ni$^{2+}$ species are predominantly present as isolated Ni$^{2+}$ cations within the ion-exchange positions.

FIG. 7(A) shows graphs of UV-vis spectra at 290K (17° C.) for (a) Ni—H—[Al]BEA, (b) Ni—Li—[Zn]BEA and (c) Ni—Li—[Al]BEA under hydrated conditions. FIG. 7(B) shows graphs of UV-vis spectra at 290K (17° C.) for (a) Ni—H—[Al]BEA, (b) Ni—Li—[Zn]BEA and (c) Ni—Li—[Al]BEA after dehydration.

Figure 8:
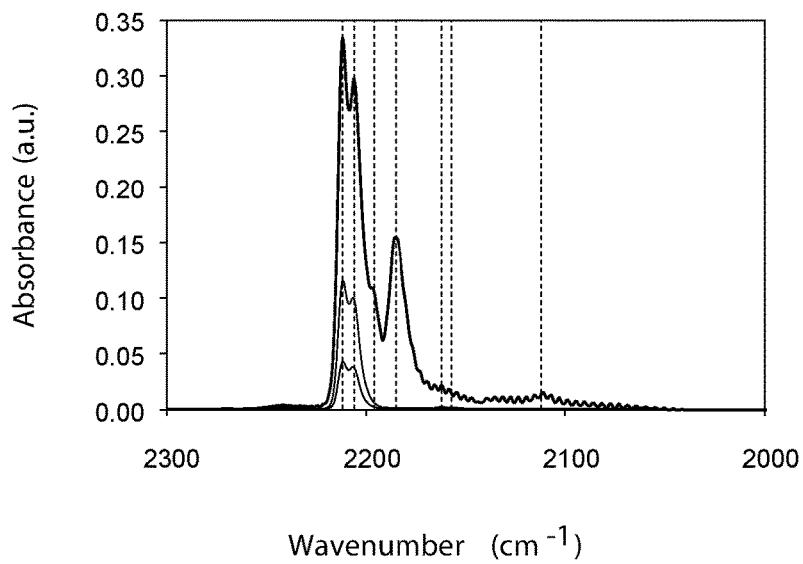
FIG. 8 is a graph of IR spectra collected for successive CO doses and saturated spectrum for Ni—Li—[Al]BEA.

CO infrared spectroscopy was performed to determine nickel speciation. Infrared spectra for Ni—Li—[Al]BEA (pretreated in air) with CO dosed sequentially and saturated at 243K (−30° C.) is shown in FIG. 8. The dashed reference lines are shown for the absorption features at 2212, 2206, 2196, 2185, 2162, 2157 and 2112 cm$^{-1}$. The saturated spectrum showed absorption bands at 2212 and 2206 cm$^{-1}$, which correspond to Ni$^{2+}$ (CO) complex formed on one kind of Ni$^{2+}$ counterion and the corresponding bicarbonyl Ni$^{2+}$ (CO)$_2$, respectively. The small shoulder at 2196 cm$^{-1}$ can be assigned to pentacoordinated Al$^{3+}$ Lewis acid sites. The peak at 2185 cm$^{-1}$ represents CO adsorbed on Li$^+$ cations and the small features observed at 2162 and 2157 cm$^{-1}$ correspond to weakly adsorbed CO on Al—OH and silanol groups, respectively. The broad feature at 2112 cm$^{-1}$ has been previously assigned to Ni$^+$(CO), indicating presence of Ni$^+$ cations. The absorption co-efficient for Ni$^+$(CO) (2112 cm$^{-1}$), however, is indicated to be 8 times higher than that for Ni$^{2+}$(CO) (2212 cm$^{-1}$). Thus, considering the relative intensities of 2112 and 2212 cm$^{-1}$ features, we conclude that only a small fraction of nickel is present as Ni$^+$ cations. These Ni$^+$ cations are likely to have formed by auto reduction of Ni$^{2+}$ cations when the sample was held at 823K (550° C.) under vacuum for 1 hour before cooling to 243K (−30° C.) under dynamic vacuum. Features at 2150 and 2030 cm$^{-1}$ for NiO and Ni$^0$ nanoparticles were absent. Therefore, CO adsorbed infrared spectroscopy confirms that nickel is predominantly present as single type of Ni$^{2+}$ counterion within the ion-exchange positions of Ni—Li—[Al]BEA.

Brønsted Acid Site Characterization

Figure 9:
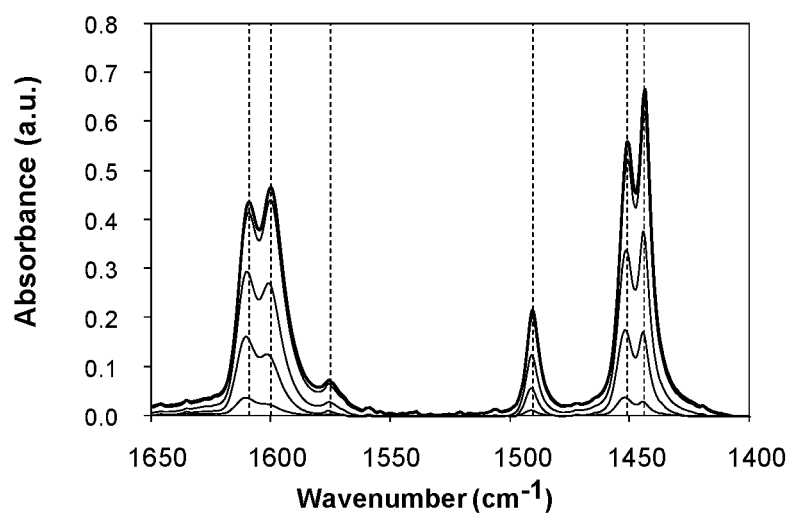
FIG. 9 is a graph of IR spectra collected for successive pyridine doses and saturated spectrum for Li—[Zn]BEA.

FIG. 9 shows evolution of IR spectra for successive doses of pyridine on Li—[Zn]BEA at 423K (150° C.). The absorption bands were observed at 1446 cm$^{-1}$ and 1575 cm$^{-1}$, which are indicative of hydrogen bonded physisorbed pyridine. The absorption bands for pyridine bound to Lewis acid sites were observed at 1451 cm$^{-1}$ and 1610 cm$^{-1}$, and another feature at 1491 cm$^{-1}$ indicated ring stretches of pyridine coordinated to Lewis acid sites or pyridine protonated at Brønsted acid sites. The characteristic IR features for protonated pyridine at 1550 and 1637 cm$^{-1}$, however, were absent, consistent with the findings of Orazov et al. Thus, Brønsted acid sites capable of protonating pyridine are absent on Li—[Zn]BEA.

Ethene Dimerization and Oligomerization Reaction Profiles

Control Materials

The control materials, Li—[Zn]BEA and Li—[Al]BEA, showed negligible reactivity for ethene (0.1-1 kPa) at 453K (180° C.), as the products formed were below the detection limit of the gas chromatograph and flame ionization detector. This suggests that under these conditions, ethene does not react with the extra framework Al present in Li—[Al]BEA, the framework Zn$^{2+}$ Lewis acid centers in Li—[Zn]BEA, and the Li$^+$ cations charge compensating the Al and Zn centers in Li—[Al]BEA and Li—[Zn]BEA, respectively.

On the other hand, the nickel exchanged catalysts Ni—H—[Al]BEA, Ni—Li—[Al]BEA, Ni—Li—[Zn]BEA, as well as H—[Al]BEA, showed ethene (0.05-1 kPa) conversion at 453K (180° C.). Conversion decreased with reaction time, as these catalysts deactivated under our experimental conditions (data not shown for all conditions). FIG. 10 shows ethene conversion for these catalysts (oxidative pretreatment) measured at 453 K, 0.4 kPa ethene pressure and at a space velocity different for each catalyst. FIG. 10(B) shows the same for Ni—Li—[Al]BEA and Ni—Li—[Al]BEA poisoned with NH$_3$ (ex-situ), with no pretreatment. For the oxidatively pretreated catalysts FIG. 10(A), the ethene conversion decreased with time for the space velocities studied, except for Ni—Li—[Zn]BEA, which exhibited an activation period. The NH$_3$ poisoned Ni—Li—[Al]BEA also exhibited an activation period, however, it showed the same conversion as un-poisoned Ni—Li—[Al]BEA after 8 hours of reaction. Thus, the activation period in this case is attributed to slow desorption of NH$_3$ from the Ni sites concurrent with catalyst deactivation, and suggests that the Ni sites are free of adsorbed NH$_3$ after 8 hours of reaction.

Figure 11:
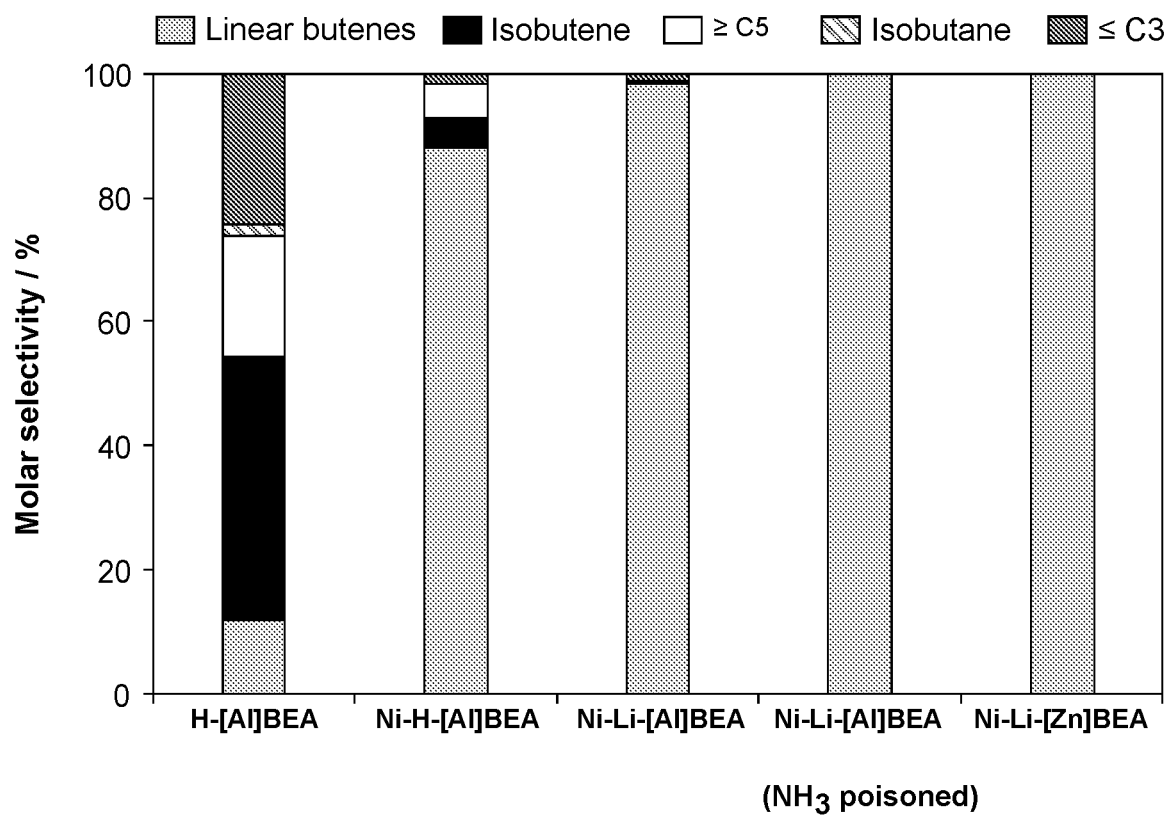
FIG. 11 is a graph of molar selectivity comparison between oxidatively pretreated H—[Al]BEA, Ni—H—[Al]BEA, Ni—Li—[Al]BEA, Ni—Li—[Zn]BEA and non-pretreated Ni—Li—[Al]BEA poisoned with $NH_3$.

FIG. 11 shows the product molar selectivity comparison for oxidatively pretreated H—[Al]BEA, Ni—H—[Al]BEA, Ni—Li—[Al]BEA at a conversion of 1.4% (FIG. 10A), Ni—Li—[Zn]BEA at a conversion of 0.035% and NH$_3$ poisoned Ni—Li—[Al]BEA at a conversion of 0.1%. The butene molar selectivity for Ni—Li—[Zn]BEA and NH$_3$ poisoned Ni—Li—[Al]BEA was found to be independent of ethene conversion and thus can be compared with that of H—[Al]BEA, Ni—H—[Al]BEA and Ni—Li—[Al]BEA at 1.4% conversion (FIG. 10A). The Ni—H—[Al]BEA catalyst showed a significantly higher selectivity towards linear butenes compared to H—[Al]BEA, and this selectivity was even higher in case of Ni—Li—[Al]BEA. This suggests that the linear butenes are predominantly formed on Ni cations, instead of on the residual H$^+$ sites.

The role of residual H$^+$ sites was investigated by comparing the molar selectivity's (FIG. 11) among the aluminosilicates. The isobutene molar selectivity was observed to be higher for H—[Al]BEA and Ni—H—[Al]BEA than for Ni—Li—[Al]BEA, suggesting that the residual H$^+$ sites are active sites for alkene skeletal isomerization. Also, the Ni—Li—[Al]BEA sample poisoned with NH$_3$ (ex-situ), showed suppressed isobutene formation and the only products detected were linear butenes. This further confirms that the residual H$^+$ sites on aluminosilicate BEA are active for alkene skeletal isomerization.

On the other hand, the absence of isobutene on Ni—Li—[Zn]BEA indicates that any residual H$^+$ sites present on the [Zn]BEA support are inactive for alkene skeletal isomerization, consistent with no IR features observed for pyridine protonated by Brønsted acid sites as shown in FIG. 9. The H—[Al]BEA catalyst also shows formation of C$_4$ alkenes, indicating that H$^+$ sites are active for ethene dimerization at 453 K on aluminosilicates. However, high molecular weight oligomers (≥C5) were also detected for Ni—H—[Al]BEA and H—[Al]BEA, but were not observed for Ni—Li—[Al]BEA and Ni—Li—[Zn]BEA, which suggests that the butenes oligomerize further on H$^+$ sites. Also, a higher selectivity towards cracking products (≤C3) was observed for H—[Al]BEA and Ni—H—[Al]BEA, suggesting cracking of butenes and higher molecular weight oligomers on the H$^+$ sites.

Figure 12:
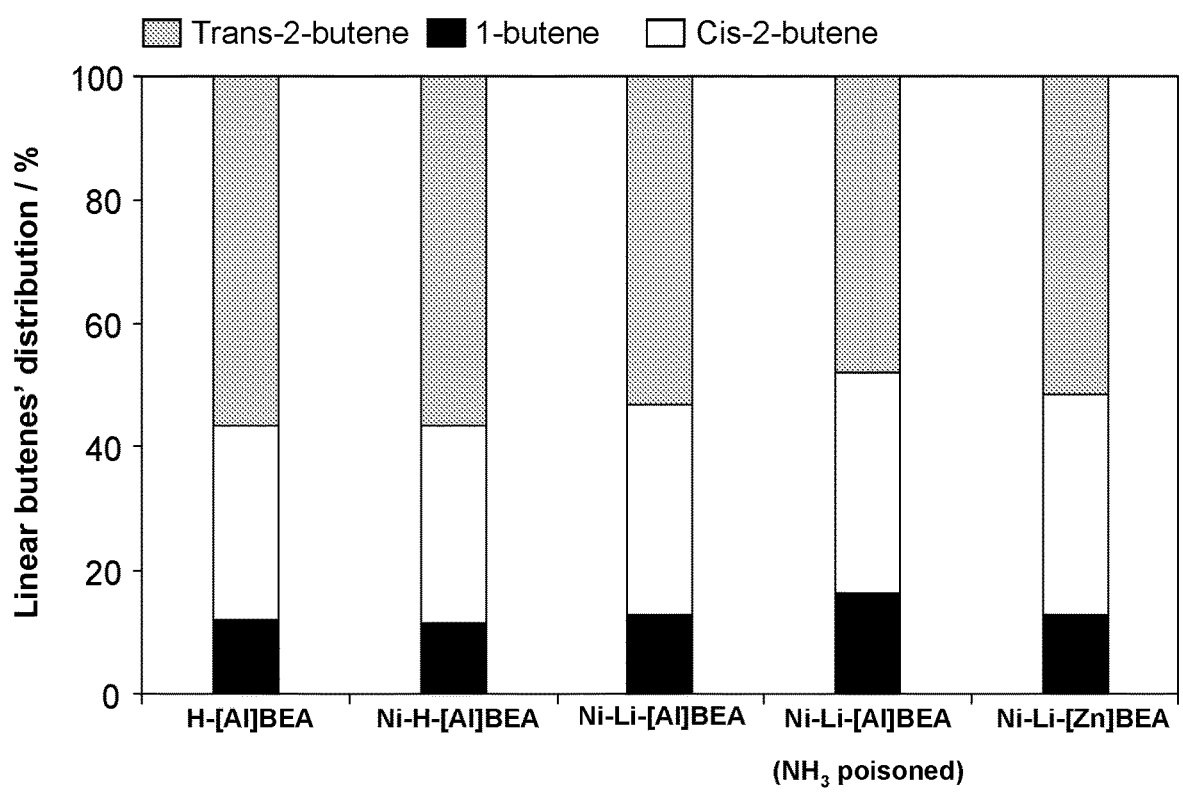
FIG. 12 is a graph of linear butene isomer distribution for oxidatively pretreated H—[Al]BEA, Ni—H—[Al]BEA, Ni—Li—[Al]BEA, Ni—Li—[Zn]BEA and non-pretreated Ni—Li—[Al]BEA poisoned with $NH_3$.)

Moreover, FIG. 12 shows the distribution among the linear butene isomers, which was observed to be identical on H—[Al]BEA and Ni—H—[Al]BEA and suggests that H$^+$ sites are active for alkene double bond isomerization. In summary, at 453K (180° C.), residual H$^+$ sites on aluminosilicate BEA are active for alkene dimerization, double bond isomerization, skeletal isomerization and mediate oligomerization and cracking reactions.

Double Bond Isomerization of Linear Butenes

As observed in FIG. 12, the distribution of linear butene isomers on Ni—H—[Al]BEA and H—[Al]BEA is identical at a given ethene conversion, and thus butene double bond isomerization on Ni cations cannot be investigated in isolation on Ni—H—[Al]BEA, given the presence of some residual H$^+$ sites.

FIG. 13 shows the transient reaction profile for 2-butenes/1-butene and isobutene/1-butene ratios for H—[Al]BEA and Ni—Li—[Al]BEA at 453 K and 0.2 kPa ethene pressure, and the transient reaction profile for 2-butenes/1-butene ratio for Ni—Li—[Zn]BEA, at 453K (180° C.) and 0.7 kPa ethene pressure. The 2-butenes/1-butene ratio for H—[Al]BEA during initial time on stream was equal to the calculated thermodynamic equilibrium value (dashed line), indicating that the linear butene isomers are equilibrated. Further, as the catalyst deactivated, the 2-butenes/1-butene ratio decreased, indicating that a non-equilibrium alkene distribution was formed. This decrease in 2-butenes/1-butene ratio was concurrent with the decrease in isobutene/1-butene ratio, and isobutene was formed in detectable amounts both when the linear butene isomers were equilibrated and non-equilibrated. Therefore, formation of isobutene serves as an indicator for butene double bond isomerization mediated by H$^+$ sites.

Figure 14:
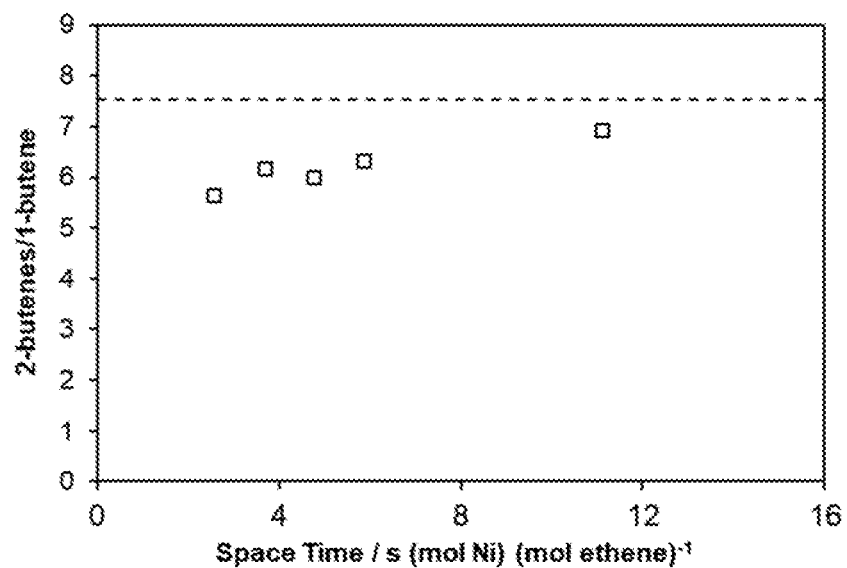
FIG. 14 is a graph of the effect of space time on 2-butenes/1-butene ratio for Ni—Li—[Al]BEA.

FIG. 13 shows that in the case of Ni—Li—[Al]BEA (at 0.39 mol ethene s$^{-1}$ (mol Ni)$^{-1}$), the linear butene isomers were not equilibrated; however, it should be noted that this initial distribution on Ni—Li—[Al]BEA is a function of ethene space time (FIG. 14). The 2-butenes/1-butene ratio for Ni—Li—[Al]BEA also decreased with reaction time, and is attributed to the deactivation of residual H$^+$ sites, because it was concurrent with the decrease in isobutene/1-butene ratio. After a long time on stream (>12 h), the 2-butenes/1-butene ratio on Ni—Li—[Al]BEA reached an asymptotic value (dash-dot line), at which there was no detectable formation of isobutene. The absence of isobutene and the non-zero asymptotic value, thus indicates that the butene double bond isomerization is mediated by the active Ni intermediates formed during the reaction and not by any H$^+$ sites. The 2-butenes/1-butene ratio for Ni—Li—[Zn]BEA also decreased with reaction time and an asymptotic value was reached, although there was no isobutene formation observed for Ni—Li—[Zn]BEA.

This decrease in 2-butenes/1-butene ratio for Ni—Li—[Zn]BEA is thought to be caused by deactivation of residual $H^+$ sites on the [Zn]BEA support which are active for butene double bond isomerization, but inactive for butene skeletal isomerization. A similar proposal has been made for Ni—Li—[Zn]BEA for propene oligomerization at 453K (180° C.), wherein the selectivity towards double-bond isomerization products decreased with reaction time. Therefore, we conclude that the Ni intermediates formed during the ethene dimerization reaction are active for butene double bond isomerization, in the absence of residual $H^+$ sites, and lead to a non-equilibrium distribution of linear butenes.

Figure 15:
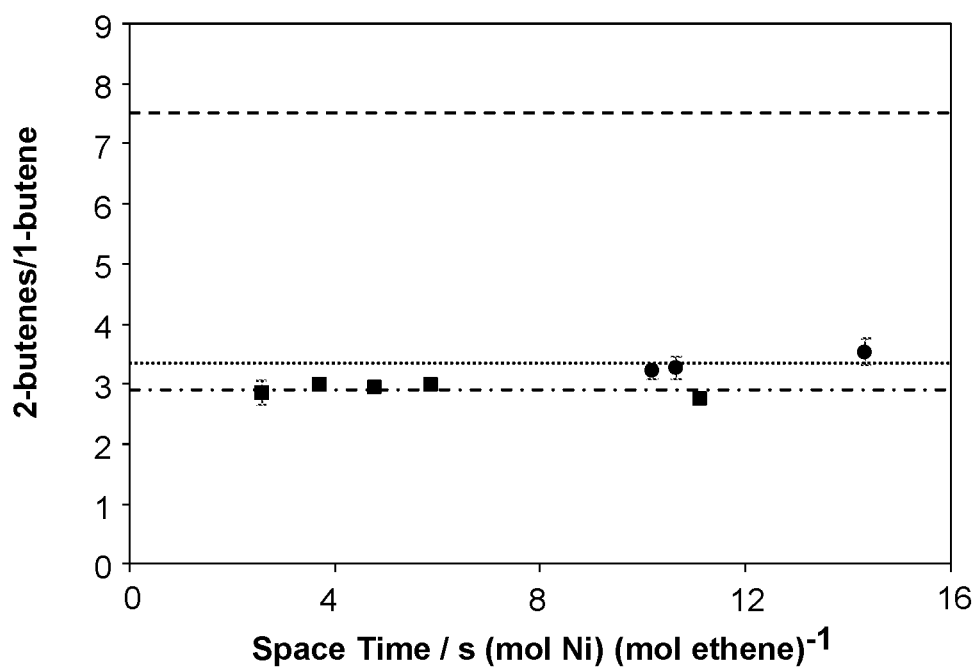
FIG. 15 is a graph of the effect of space time on non-equilibrium distribution of linear butene isomers on Ni intermediates for Ni—Li—[Al]BEA and Ni—Li—[Zn]BEA.

FIG. 15 shows the effect of space time on this non-equilibrium distribution at 453K (180° C.) for Ni—Li—[Al]BEA (0.2 kPa ethene) and Ni—Li—[Zn]BEA (0.7 kPa ethene). For both Ni—Li—[Al]BEA and Ni—Li—[Zn]BEA, this non-equilibrium distribution was observed, and was invariant with space time, which provides direct evidence for double bond isomerization on Ni intermediates via a primary reaction pathway. This important mechanistic detail is consistent with the Cossee-Arlman mechanism and not with the metallacycle mechanism, proposed for ethene dimerization on homogenous Ni-based catalysts [65-67]. Therefore, we conclude the Cossee-Arlman mechanism to be the dominant route for ethene dimerization on Ni cations, in agreement with some experimental and theoretical proposals for Ni cations confined within microporous aluminosilicates and MOFs.

Previous studies on ethene oligomerization report that the 1-butene selectivity decreases with increasing density of $H^+$ sites (decreasing Si/Al ratio) and with increasing temperature (323-423K) (50-150° C.) for Ni—H—[Al]MCM-41, Ni—H—[Al]MCM-22, Ni—H—[Al]MCM-36 and Ni—H—[Al]USY. Additionally, for ethene oligomerization on Ni—H—[Al]SBA-15, they report that the 1-butene selectivity decreases (77% to 16%) with an increase in temperature (323-423K) (50-150° C.), an increase in residence time and an increase in ethene conversion, and thereby claim that 1-butene is the primary product of ethene oligomerization formed on the Ni sites and further undergoes double bond isomerization on the $H^+$ sites. Our observation of double bond isomerization products at 453K (180° C.) on Ni—Li—[Al]BEA and Ni—Li—[Zn]BEA after deactivation of the residual $H^+$ sites and on Ni—Li—[Al]BEA pre-poisoned with $NH_3$, together with the lower-than-equilibrium 2-butenes/1-butene ratios formed on these materials, suggests that double-bond isomerization occurs on the active Ni intermediates in addition to the residual $H^+$ sites. Our findings are in agreement with those of Ng and Creaser [F. T. T. Ng, D. C. Creaser, Ethylene dimerization over modified nickel exchanged Y-zeolite, App. Catal., A, 119 (1994) 327-339], who reported that the 1-butene selectivity (after 8 hours) is similar for Ni—H—[Al]Y and Ni—H—[Al]Y samples modified with NaOH, $NH_3$ and pyridine to poison the residual $H^+$ sites, and thus the Ni sites are active for double bond isomerization of linear butenes.

Formation of Cossee-Arlman Active Site

For Ni—Li—[Al]BEA and Ni—Li—[Zn]BEA, after treatment in an oxidizing environment, nickel is predominantly present as $Ni^{2+}$ cations in a single type of ion-exchange site as evidenced by elemental analysis, UV-vis spectroscopy and CO adsorbed IR spectroscopy. The formation of active site starting from these isolated $Ni^{2+}$ cations was studied by measuring the transient net butene formation rate on Ni—Li—[Al]BEA and Ni—Li—[Zn]BEA at 453 K (180° C.). The net butene formation transient at 453K (180° C.) for Ni—Li—[Al]BEA (0.1 kPa) and Ni—Li—[Zn]BEA (0.4 kPa) during initial time on stream is plotted in FIG. 16A. We observed that both the catalysts exhibited an activation period, wherein the net butene formation rate increased to a maximum value, following which the catalysts continued to deactivate. Further, FIG. 16B shows the duration of this activation period as a function of ethene pressure at 453K (180° C.), and this duration was observed to decrease with increase in ethene pressure for both Ni—Li—[Al]BEA and Ni—Li—[Zn]BEA. Based on these observations, we conclude that the activation period represents formation of dimerization active site by interaction of isolated $Ni^{2+}$ cations with ethene, in absence of a co-catalyst.

For Ni—H—[Al]BEA (393K (120° C.), 26 bar of ethene pressure, 35 bar total pressure), however, no activation period has been reported. This is likely because the activation period is expected to be undetectable at such high ethene pressures, given our observations for Ni—Li—[Al]BEA at 453K (180° C.) (FIG. 10B). A similar activation period has also been reported by Mlinar et. al [A. N. Mlinar, G. B. Baur, G. G. Bong, A. B. Getsoian, A. T. Bell, Propene oligomerization over Ni-exchanged Na—X zeolites, Journal of Catalysis, 296 (2012) 156-164], for propene oligomerization on Ni—Na—[Al]X at 453K (180° C.), wherein the duration of activation period decreased with increase in propene pressure and with increase in Ni loading at a fixed WHSV. This is attributed to the assisted migration of $Ni^{2+}$ cations out of the hexagonal prisms of FAU, as the migration of one $Ni^{2+}$ cation out of the hexagonal prism relaxes the distorted hexagonal prism which promotes migration of adjacent $Ni^{2+}$ cations as previously reported for $Ni^{2+}$ reduction in Na—[Al]X and observed in a DFT study. In their studies, it is hypothesized that the activation period is comprised of migration of $Ni^{2+}$ cations from the hexagonal prisms of FAU to the sodalite cages and their coordination with propene to form a $Ni^{2+}$-propene complex which is indicated to be a $Ni^{2+}$—$(C_3H_6)_2$ complex according to a reaction model fitted to their kinetic data. For propene oligomerization on Ni—Li—[Zn]BEA (453K (180° C.), 85 kPa propene pressure), however, no activation period has been reported, which is likely because the catalyst was pretreated in an oxidant free environment and the high propene partial pressure used would have diminished the activation period. Thus, we hypothesize that the activation period for Ni—Li—[Al]BEA involves coordination of two ethene molecules to an isolated $Ni^{2+}$ cation to form a $Ni^{2+}$—$(C_2H_4)_2$ complex which is then likely transformed into the purported active site for ethene dimerization. Also, the BEA framework is made up of composite building units BEA, MOR and MTW, and Ni cations exchanged on any pair of tetrahedral framework Al atoms within the network of these building units is accessible either through the 12-MR or through 6-MR channels created by the mtw building units. Thus, for Ni—Li—[Al]BEA, the migration of $Ni^{2+}$ cations on exposure to ethene at 453K (180° C.) is unlikely.

Accordingly, a theoretical study by Brogaard and Olsbye [R. Y. Brogaard, U. Olsbye, Ethene Oligomerization in Ni-Containing Zeolites: Theoretical Discrimination of Reaction Mechanisms, ACS Catal., 6 (2016) 1205-1214] have proposed a reaction pathway for formation of Cossee-Arlman active site by interaction of isolated $Ni^{2+}$ cations with ethene, in absence of a co-catalyst. The proposed pathway involves coordination of two ethene molecules to an isolated $Ni^{2+}$ cation, deprotonation to the framework forms a $[Ni^{2+}$-butenyl$]^+$ species which is displaced along the framework, rotation forms an agostically bound $[Ni^{2+}$-butadiene-H$]^+$, and finally 1,3-butadiene desorbs by chain transfer pathway involving adsorption of another ethene and β-hydride transfer to form the ethene coordinated $[Ni^{2+}$—H$]^+$ species (Cossee-Arlman active site). Thus, along with the Cossee-Arlman active site, the proposed pathway suggests formation of a proximal $H^+$ site and 1,3-butadiene.

As discussed above, the residual $H^+$ sites on an aluminosilicate BEA are active for butene double bond isomerization and butene skeletal isomerization. Thus, the net butene formation transient on Ni—Li—[Al]BEA under conditions of low ethene pressure (0.05 kPa) is compared with the transients for 2-butenes/1-butene and isobutene/1-butene in FIGS. 17A and 17B, respectively. The increase in net butene formation rate during the activation period was accompanied by a corresponding increase in the 2-butenes/1-butene ratio (FIG. 17A) and the isobutene formation rate (FIG. 17B). It should be noted that the double bond isomerization on Ni intermediates proceeds via a primary reaction pathway and thus is independent of net butene formation rate, whereas the double bond isomerization on $H^+$ sites proceeds via a secondary reaction pathway and thus the 2-butenes/1-butene ratio is a function of the net butene formation rate. Therefore, the observations in FIGS. 17A and 17B suggest the formation of dimerization active site is accompanied by formation of proximal $H^+$ sites, which increases the isobutene formation rate and the extent of double bond isomerization.

Figure 17:
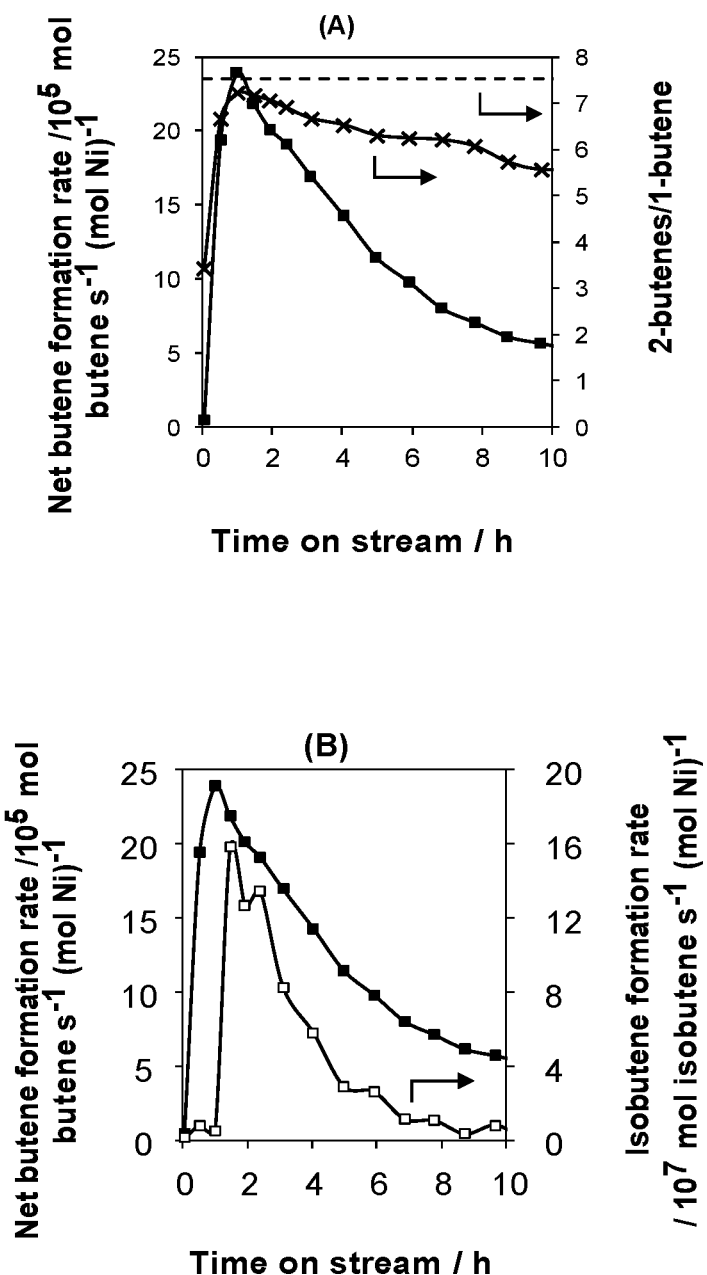
FIG. 17 are graphs of (A) Transient net butene formation rate and 2-butenes/1-butene ratio for Ni—Li—[Al]BEA. (B) Transient net butene formation rate and isobutene formation rate for Ni—Li—[Al]BEA.
Figure 18:
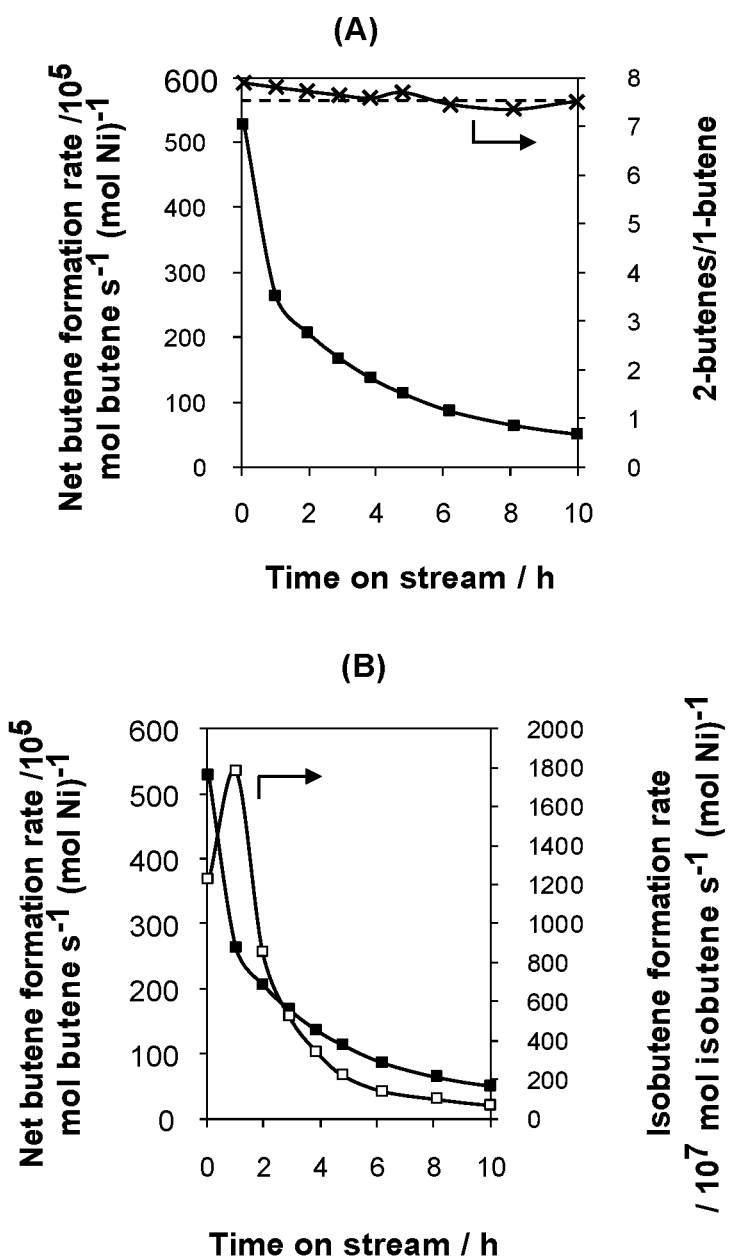
FIG. 18 are graphs of (A) Comparison between the transients for net butene formation rate and 2-butenes/1-butene ratio. (B) Comparison between the transients for net butene formation rate and isobutene formation rate.
Figure 19:
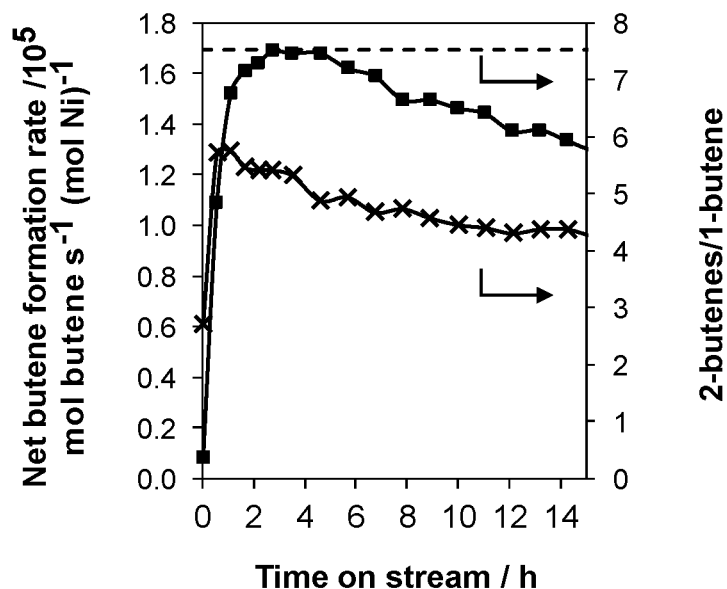
FIG. 19 is a graph showing a comparison between the transients for net butene formation rate and 2-butenes/1-butene ratio.

Referring to FIG. 18, preliminary experiments with Ni—H—[Al]BEA catalyst did not show the same correspondence for the transients as in FIG. 17, thus allowing us to disregard the presence of a minority amount of $H^+$ sites on the fresh catalyst. Therefore, the concurrent behavior of the transients for 2-butene/1-butene ratio, the isobutene formation rate and the net butene formation rate, allow us to conclude the concurrent formation of proximal $H^+$ sites with the dimerization active site during the activation period. This behavior is not observed in the case of Ni—Li—[Zn]BEA catalyst, as seen in FIG. 19, thus indicating that the activation of this catalyst occurs by a different reaction pathway.

Mechanistic Considerations for the Cossee-Arlman Pathway

Brogaard and Olsbye [R. Y. Brogaard, U. Olsbye, Ethene Oligomerization in Ni-containing Zeolites: Theoretical Discrimination of Reaction Mechanisms, ACS Catal., (2016)] have computed a free energy profile for the Cossee-Arlman pathway on isolated $Ni^{2+}$ cations in a SSZ-24 framework for ethene dimerization at 393K (120° C.) and 1 bar ethene pressure. The free energy profile shows the formation of the β-agostic butyl complex from nickel-ethyl-ethene species (Step 3, Scheme 1) to involve a free energy barrier of 68 kJ $mol^{-1}$, which is the highest intrinsic free energy barrier within this free energy profile.

Thus, considering this step to be the kinetically relevant step, and other steps to be quasi-equilibrated (Scheme 1), the following rate expression was derived (Equation 1) for ethene dimerization ($r_D$=Ethene dimerization rate normalized to the Cossee-Arlman active site).

$$r_D = \frac{k_3 K_2 K_1 P_{C2H4}}{1 + K_1 + K_2 K_1 P_{C2H4}} \qquad (1)$$

Scheme 1. Proposed Cossee-Arlman reaction pathway with mechanistic assumptions

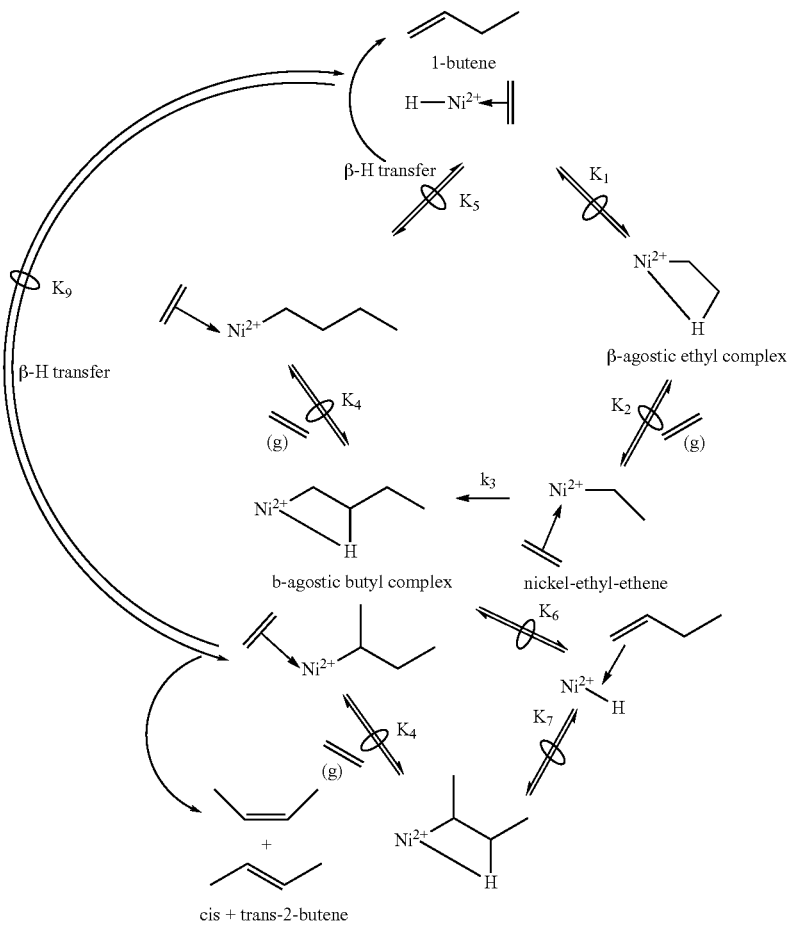

In this equation, $K_i$ is the equilibrium constant for the quasi-equilibrium between the Cossee-Arlman active site and the β-agostic butyl complex, $K_2$ is the equilibrium constant relating the concentrations of β-agostic ethyl complex and nickel-ethyl-ethene species to the extrazeolite ethene pressures and $k_3$ is the rate constant for the step of formation of the β-agostic butyl complex from the nickel-ethyl-ethene species. Thus, the coverage terms (from left to right) in equation (1) correspond to the Cossee-Arlman active site, the β-agostic ethyl complex and the nickel-ethyl-ethene species. The β-agostic ethyl complex is reported to adopt a structure that approximates a square planar geometry around Ni(II), while the nickel-ethyl-ethene species is reported to adopt a tetrahedral orientation which is less hindered intrinsically. Ni(II), however, is a $d^8$ system and it prefers square planar geometry when coordinated to strong field ligands like hydride or alkyl. In agreement with this, the calculated free energy barriers by Brogaard and Olsbye [R. Y. Brogaard, U. Olsbye, Ethene Oligomerization in Ni-Containing Zeolites: Theoretical Discrimination of Reaction Mechanisms, ACS Catal., 6 (2016) 1205-1214] indicate the β-agostic ethyl complex to be relatively more stable among the three coverage terms, and thus can be considered as the most abundant surface intermediate (MASI). This assumption of MASI, simplified equation (1) into a first order rate law, as given below.

$$r_D = k_3 K_2 P_{C2H4} = k_{app} P_{C2H4} \quad (2)$$

In this equation, $k_{app}$ is the effective first order ethene dimerization rate constant.

Kinetics of Ethene Dimerization on Nickel Cations

The net butene formation rate measured at 453K (180° C.) for Ni—Li—[Al]BEA and Ni—Li—[Zn]BEA exhibited an activation transient (<0.4 kPa for Ni—Li—[Al]BEA, 0.1-1 kPa for Ni—Li—[Al]BEA) along with a deactivation transient (0.05-1 kPa ethene). Treatment of the used catalysts at 773K (500° C.), regenerated the catalysts partially under helium flow, and completely under 5% 02/He flow. This suggests that the catalyst deactivation is mainly caused by formation of high molecular weight oligomers on Ni cations, which have been reported to form by secondary reactions of product butenes. It should be noted that the observed activation transient represents combined activation and deactivation processes, and because the rate of active site formation exceeds the rate of deactivation, the net butene formation rate was observed to increase. On the other hand, the deactivation transient only represents the catalyst deactivation process. Thus, the initial net butene formation rate for both catalysts was estimated by extrapolating the deactivation transient data to zero time on stream.

Figure 21:
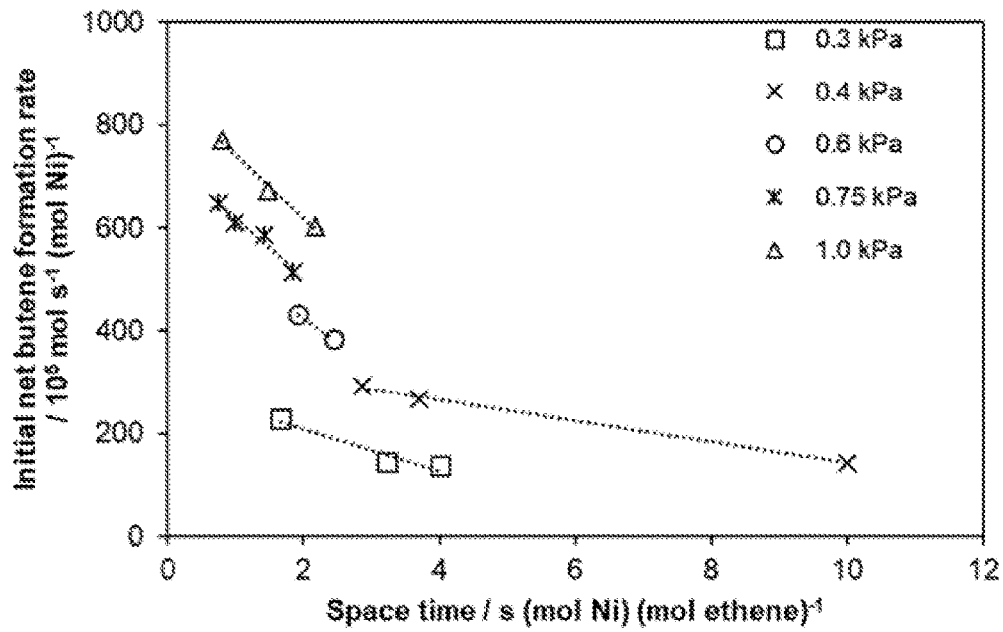
FIG. 21 is a graph of the effect of gas space velocity or residence time on initial net butene formation rate on Ni—Li—[Al]BEA at various ethene pressures.
Figure 22:
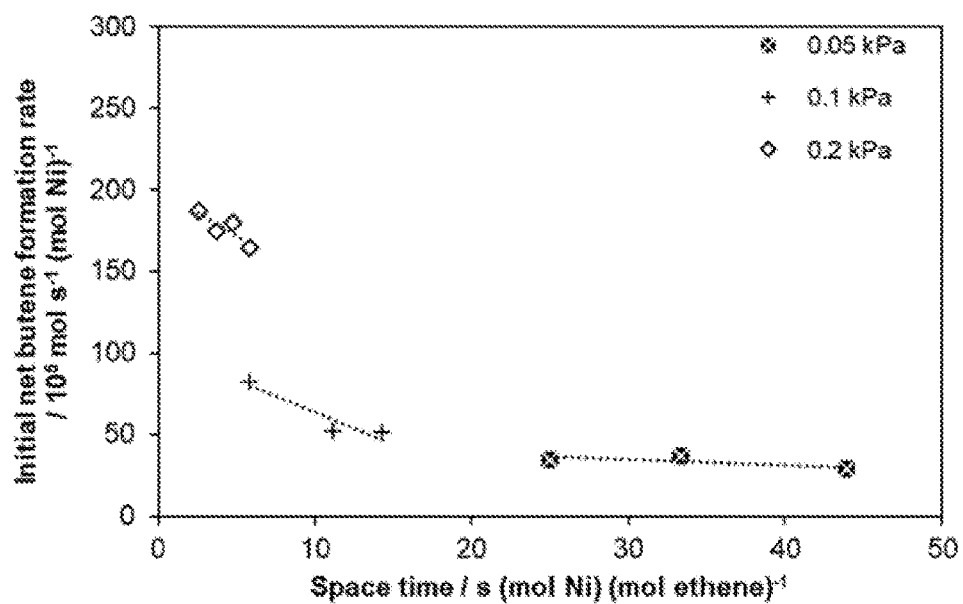
FIG. 22 is a graph of the effect of space time on initial net butene formation rate on Ni-Li-[Al]BEA at various ethene pressures.

The deactivation transient for both Ni—Li—[Al]BEA and Ni—Li—[Zn]BEA was found to be well described by a hyperbolic deactivation model. For Ni—Li—[Al]BEA at 453K (180° C.), a hyperbolic deactivation model was fitted to the initial transient of the measured net butene formation rate as shown in FIG. 20. Further, the initial net butene formation rate measured for Ni—Li—[Al]BEA at a given ethene partial pressure, increased linearly with decrease in space time, as shown in FIG. 21, which is attributed to suppressed secondary reactions of product butenes to form high molecular weight oligomers, leading to deactivation of active Ni intermediates. This linear trend for initial net butene formation rates was extrapolated to zero space time to determine the initial butene formation rate, or simply the initial ethene dimerization rate.

Figure 23:
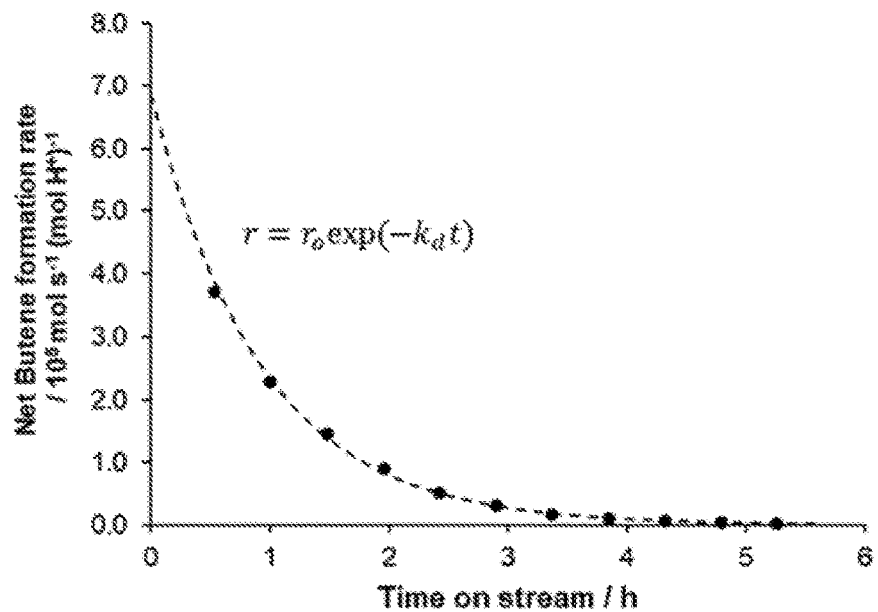
FIG. 23 is a graph of the net butene formation rate for H—[Al]BEA fitted with an exponential deactivation model.

Proximal $H^+$ sites are formed on Ni—Li—[Al]BEA during the formation of Cossee-Arlman active site, which are also active for ethene dimerization when present on [Al] BEA supports. The initial ethene dimerization rate per $H^+$ site was estimated on a control material of H—[Al]BEA in the same manner as Ni—Li—[Al]BEA. Referring now to FIG. 23, net butene formation rate for H—[Al]BEA at 453K (180° C.), 0.2 kPa ethene and 0.008 mol ethene (mol $H^+$)$^{-1}$ s$^{-1}$ is fitted with an exponential deactivation model. $r_o$ is the initial net butene formation rate, $k_d$ is the apparent first order deactivation rate constant and t is time in h. The initial net butene formation rate (453K (180° C.), 0.2 kPa ethene) on H—[Al]BEA was extrapolated to zero space time (FIG. 24) to determine the initial ethene dimerization rate of 8.76× 10$^{-5}$ mol s$^{-1}$ (mol $H^+$)$^{-1}$. On the other hand, for Ni—Li—[Al]BEA at 453K (180° C.) and 0.2 kPa ethene pressure, the initial ethene dimerization rate was determined to be 2.03× 10$^{-3}$ mol s$^{-1}$ (mol Ni)$^{-1}$ from FIG. 21. Therefore, the turnover rate for ethene dimerization on $H^+$ sites is two orders of magnitude lower than that on $Ni^{2+}$ sites. Therefore, the contribution from the proximal $H^+$ sites generated during the catalyst activation to the initial ethene dimerization rate determined for Ni—Li—[Al]BEA can be neglected.

Figure 24:
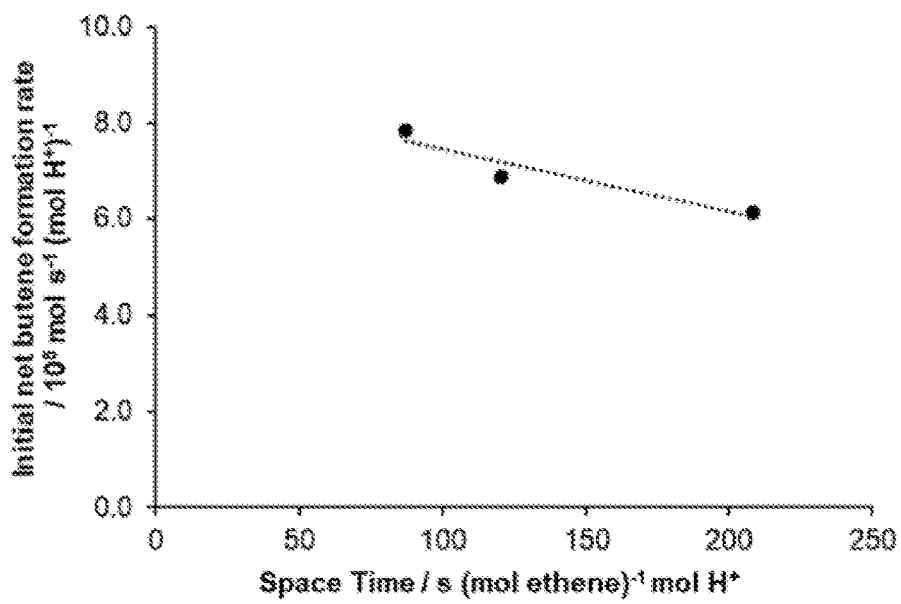
FIG. 24 is a graph of the effect of space time on initial net butene formation rate for H—[Al]BEA.
Figure 25:
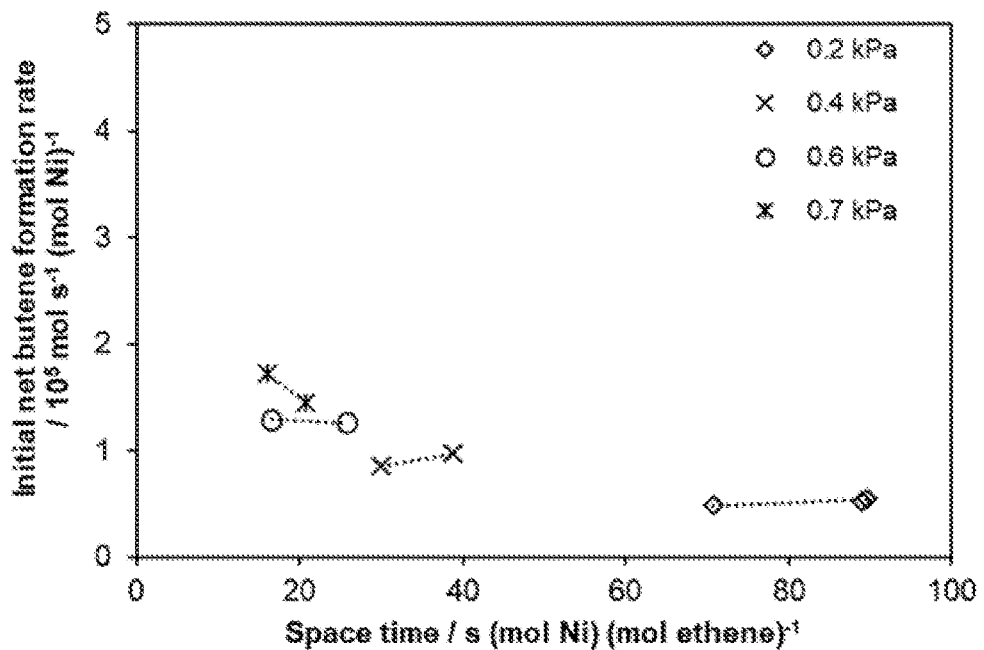
FIG. 25 is a graph of the effect of gas space velocity or residence time on initial net butene formation rate on Ni—Li—[Zn]BEA at various ethene pressures.

For Ni—Li—[Zn]BEA, the initial net butene formation rate at 453K (180° C.) and at a given ethene partial pressure was observed to be invariant with space time, as shown in FIG. 24. Thus, the initial ethene dimerization rate on Ni—Li—[Zn]BEA was determined as the mean value of initial net butene formation rates, invariant with space time. The effect of gas space velocity or residence time on initial net butene formation rate on Ni—Li—[Zn]BEA at 453K (180° C.) and ethene pressures of: 0.2, 0.4, 0.6, 0.7 and 1 kPa is shown in FIG. 25.

Figure 26:
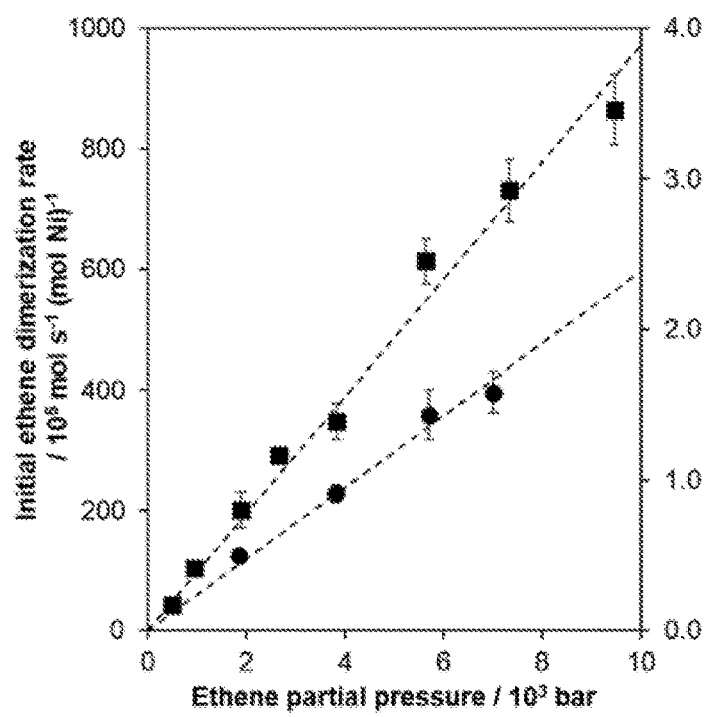
FIG. 26 is a graph of the dependence of initial ethene dimerization rate on Ni—Li—[Al]BEA and Ni—Li—[Zn]BEA on the ethene pressure.

The initial ethene dimerization rates determined on Ni—Li—[Al]BEA and Ni—Li—[Zn]BEA at 453K (180° C.), show a first order dependence (FIG. 26) on ethene partial pressure (0.05-1 kPa), consistent with the mechanism derived rate expression (Equation 2). Thus, the measured kinetic data is consistent with the mechanistic assumptions of the kinetically relevant step being the formation of β-agostic butyl complex from nickel-ethyl-ethene species and the β-agostic ethyl complex being the most abundant surface intermediate (MASI). This agrees with the work by Ng and Creaser [F. T. T. Ng, D. C. Creaser, Ethylene Dimerization: Kinetics and Selectivity for 1-Butene, in: J. S. Kevin, C. S. Emerson (Eds.) Studies in Surface Science and Catalysis, Elsevier, 1992, pp. 123-131], who have reported for Ni—Na—[Al]Y at 323-343K, a first order dependence of ethene dimerization rate on ethene pressures of 7-40 bar. Also Mlinar et al. [A. N. Mlinar, O. C. Ho, G. G. Bong, A. T. Bell, The Effect of Noncatalytic Cations on the Activity and Selectivity of Nickel-Exchanged X Zeolites for Propene Oligomerization, ChemCatChem, 5 (2013) 3139-3147]] have reported first order dependence of propene dimerization rate at 453K (180° C.) on Ni—[Al]X materials for propene pressures 1-5 bar.

On all Ni-zeolites studied, ethene dimerization rates increased with time-on-stream (activation period) to a maximum value, and then decreased with further time-on-stream (deactivation period). This transient activation period reflects structural changes to isolated $Ni^{2+}$ cations to form the dimerization active site, the structural details of which are currently under investigation. Only 1-butene, cis-2-butene and trans-2-butene were formed on catalysts containing only Ni sites, while isobutene and $C_3$ and $C_5$+ hydrocarbons were formed on catalysts also containing residual $H^+$ sites. Thus, double bond isomerization of butenes can occur on $Ni^{2+}$ sites alone. This is an important mechanistic detail that is imprecisely understood in the experimental literature for ethene dimerization on Ni-exchanged oxides, with the majority of proposals suggesting that Ni sites form 1-butene and that residual H$^+$ sites catalyze double bond isomerization.

Effect of Framework Heteroatom

The measured first order dimerization rate constants at 453 K (180° C.) for Ni—Li—[Al]BEA and Ni—Li—[Zn]BEA are 0.97 and 0.002 (mol butene) s$^{-1}$ (mol Ni)$^{-1}$ bar$^{-1}$, respectively. These differences in the rate constants measured at active Ni species formed at two framework Al sites or at one framework Zn site, reflect the differences in the ethene adsorption energies or intrinsic dimerization activation enthalpies. The UV-vis spectroscopy under dehydrated conditions showed structural differences between the Ni$^{2+}$ cations on Ni—Li—[Al]BEA and Ni—Li—[Zn]BEA, where they were present in a tetrahedral and octahedral coordination environment, respectively. Further, during ethene dimerization at 453K (180° C.), the cis-2-butene/trans-2-butene ratio measured on Ni$^{2+}$ intermediates for Ni—Li—[Al]BEA was 0.8, while that for Ni—Li—[Zn]BEA was 0.6, and this distribution among internal butenes was independent of ethene pressure and space velocity for both the catalysts. It is proposed that the identity of framework heteroatom (Al$^{3+}$, Zn$^{2+}$) influences the intrinsic reactivity of the charge compensating Ni$^{2+}$ cations for ethene dimerization.

An embodiment of the present disclosure is a catalyst composition for the oligomerization of light olefins that includes a Group VIII metal selected from the group consisting of nickel, iron, cobalt, and combinations thereof, and a support. The Group VIII metal can be present in an amount ranging from 0.1 wt % to 10 wt % on an elemental basis of the catalyst composition. In an embodiment the support is selected from the group consisting of molecular sieves and zeolites. In an embodiment the support is selected from the group consisting of aluminosilicates and zincosilicates. In an embodiment the support is treated for H$^+$ sites, such as by selective poisoning. In an embodiment the selective poisoning comprises addition of NH$_3$. In an embodiment the treatment for H$^+$ sites is their replacement with Li$^+$ cations. In an embodiment the Ni is in the form of Ni$^{2+}$ cations. In an embodiment the Ni is coordinated with two framework heteroatom Al$^{3+}$ centers in a paired configuration. In an embodiment the Ni is coordinated with one framework heteroatom Zn$^{2+}$ center. In an embodiment the catalyst is efficacious in catalysis of oligomerization reactions of light olefins, such as ethene dimerization and/or propene dimerization.

An embodiment of the present disclosure is a process for the oligomerization reactions of light olefins comprising: providing a catalyst as described above; contacting the catalyst with a feedstream comprising $C_2$ to $C_5$+ alkenes under oligomerization conditions; and oligomerization reaction occurs converting a portion of the $C_2$ to $C_5$+ alkenes to $C_4$ to $C_6$+ olefins. In an embodiment the conversion of $C_2$ to $C_5$+ alkenes to $C_4$ to $C_6$+ olefins is at least 5%. In an embodiment the feedstream comprises of ethene and selectivity of ethene to butene is greater than 90%. In an embodiment the conversion of ethene to butene is at least 5% with selectivity of ethene to butene greater than 90%. In an embodiment the conversion of ethene to butene is at least 5% with selectivity of ethene to butene is greater than 90% and the reaction continues for at least 30 minutes, optionally at least 1 hour, optionally at least 2 hours, optionally at least 5 hours, optionally at least 10 hours, optionally at least 15 hours.

An embodiment of the present disclosure is a method of making an oligomerization catalyst comprising: providing a support material; adding to the support material a Group VIII metal selected from the group consisting of nickel, iron, cobalt, and combinations thereof; and calcining the catalyst material to form an oligomerization catalyst. In an embodiment the Group VIII metal is nickel and is present in an amount ranging from 0.1 wt % to 10 wt % on an elemental basis of the oligomerization catalyst composition. In an embodiment the support is selected from the group consisting of molecular sieves and zeolites. In an embodiment the support is selected from the group consisting of aluminosilicates and zincosilicates. In an embodiment the method includes treating the catalyst for H$^+$ sites. In an embodiment the treatment for H$^+$ sites is selective poisoning. In an embodiment the selective poisoning comprises addition of NH$_3$. In an embodiment the treatment for H$^+$ sites is their replacement with Li$^+$ cations. In an embodiment Ni on the catalyst is Ni$^{2+}$ cations. In an embodiment the Ni$^{2+}$ is coordinated with two framework heteroatom Al$^{3+}$ centers in a paired configuration. In an embodiment the Ni$^{2+}$ is coordinated with one framework heteroatom Zn$^{2+}$ center.

An embodiment of the present disclosure is a catalyst composition for the oligomerization of light olefins comprising: nickel present in the form of Ni$^{2+}$ cations in an amount ranging from 0.1 wt % to 10 wt % on an elemental basis of the catalyst composition; and a molecular sieve support having framework heteroatoms selected from the group consisting of Al$^{3+}$, Zn$^{2+}$, and combinations thereof; wherein the Ni$^{2+}$ cations are coordinated with two framework Al$^{3+}$ heteroatom centers in a paired configuration or with one framework Zn$^{2+}$ heteroatom center, or combinations thereof and the catalyst is treated for H$^+$ sites by replacing them with Li$^+$ cations.

The text above describes one or more specific embodiments of a broader disclosure. The disclosure also can be carried out in a variety of alternate embodiments and thus is not limited to those described here. The foregoing description of an embodiment of the disclosure has been presented for the purposes of illustration and description. It is not intended to be exhaustive or to limit the disclosure to the precise form disclosed. Many modifications and variations are possible in light of the above teaching. It is intended that the scope of the disclosure be limited not by this detailed description, but rather by the claims appended hereto.

What is claimed is:

1. A process for the oligomerization reactions of light olefins comprising:
   contacting a Group VIII metal selected from the group consisting of nickel, iron, cobalt, and combinations thereof with a support having H+ sites to provide a supported catalyst, the support selected from the group consisting of silica, silicon dioxide, titanium dioxide, metal modified silica, silica-pillared clays, silica-pillared micas, metal oxide modified silica-pillared mica, silica-pillared tetrasilicic mica, silica-pillared taeniolite, zeolite, molecular sieve, and combinations thereof;
   calcining the supported catalyst,
   contacting the calcined supported catalyst with NH$_3$ to remove residual H+ sites, and then
   contacting the treated catalyst with a feedstream comprising one or more $C_2$ to $C_{5+}$ alkenes at reaction conditions sufficient to provide a product comprising one or more $C_4$ to $C_{6+}$ olefins.

2. The process according to claim 1 wherein the Group VIII metal is nickel.

3. The process according to claim 1 wherein the Group VIII metal is present in an amount ranging from 0.001 wt % to 25 wt % on an elemental basis of the catalyst.

4. The process according to claim 1 wherein the support is selected from the group consisting of molecular sieves and zeolites.

5. The process according to claim 1 wherein the metal modified silica is selected from the group consisting of aluminosilicates and zincosilicates.

6. The process according to claim 2 wherein the nickel comprises $Ni^{2+}$ cations.

7. The process according to claim 2 wherein the nickel is coordinated with two framework heteroatom $Al^{3+}$ centers in a paired configuration or coordinated with one framework heteroatom $Zn^{2+}$ center.

8. The process according to claim 1 further comprising treating the support with $Li^+$ or both prior to contacting with the Group VIII metal.

9. The process according to claim 1, wherein the one or more $C_4$ to $C_{6+}$ olefins are linear.

10. A process for the oligomerization reactions of light olefins comprising:
   contacting a nickel containing compound and a zeolite to provide a supported catalyst;
   calcining the supported catalyst,
   treating the supported catalyst by selective poisoning $H^+$ sites using $NH_3$, and then
   contacting the treated supported catalyst with a feedstream comprising one or more $C_2$ to $C_{5+}$ alkenes at reaction conditions sufficient to provide a product comprising one or more $C_4$ to $C_{6+}$ olefins.

11. The process according to claim 10, wherein the nickel is present in an amount ranging from 0.001 wt % to 25 wt % on an elemental basis of the catalyst.

12. The process according to claim 10, wherein the nickel comprises $Ni^{2+}$ cations.

13. The process according to claim 10, wherein the zeolite is an aluminosilicate or zincosilicate having a BEA topology.

14. The process according to claim 10, wherein the nickel is coordinated with two framework heteroatom $Al^{3+}$ centers in a paired configuration or coordinated with one framework heteroatom $Zn^{2+}$ center.

15. The process according to claim 10, further comprising treating the zeolite with a Brønsted base comprising Li+ prior to contacting the zeolite with nickel.

16. The process according to claim 10, wherein the product comprising one or more $C_4$ to $C_{6+}$ olefins consists essentially of one or more linear $C_4$ to $C_{6+}$ olefins.

17. The process according to claim 10, wherein the one or more $C_4$ to $C_{6+}$ olefins are linear.

18. A process for the oligomerization reactions of light olefins comprising:
   treating a zeolite with $Li^+$ to remove residual $H^+$ sites,
   contacting the treated zeolite with a Group VIII metal selected from the group consisting of nickel, iron, cobalt, and combinations thereof to provide a supported catalyst; and then
   contacting the supported catalyst with a feedstream comprising one or more $C_2$ to $C_{5+}$ alkenes at reaction conditions sufficient to provide a product consisting essentially of linear $C_4$ to $C_{6+}$ olefins.

19. The process according to claim 18 wherein the Group VIII metal is nickel.

20. The process according to claim 19 wherein the nickel is present in an amount ranging from 0.001 wt % to 25 wt % on an elemental basis of the catalyst.

21. The process according to claim 18 wherein the zeolite is an aluminosilicate.

22. The process according to claim 18 wherein the zeolite is a zincosilicate.

23. The process according to claim 19 wherein the nickel comprises $Ni^{2+}$ cations.

24. The process according to claim 23 wherein the nickel is coordinated with two framework heteroatom $Al^{3+}$ centers in a paired configuration or coordinated with one framework heteroatom $Zn^{2+}$ center.

25. The process according to claim 18 wherein the Brønsted base comprises $Li^+$.

26. The process according to claim 18 further comprising treating the supported catalyst by selective poisoning residual $H^+$ sites using a Brønsted base.

27. The process according to claim 26 wherein the Bronsted base is $NH_3$.

* * * * *